(12) United States Patent
Julien et al.

(10) Patent No.: US 6,410,301 B1
(45) Date of Patent: Jun. 25, 2002

(54) MYXOCOCCUS HOST CELLS FOR THE PRODUCTION OF EPOTHILONES

(75) Inventors: Bryan Julien, Oakland; Leonard Katz, Hayward; Chaitan Khosla, Palo Alto, all of CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/560,367

(22) Filed: Apr. 28, 2000

Related U.S. Application Data

(63) Continuation-in-part of application No. 09/443,501, filed on Nov. 19, 1999, now Pat. No. 6,303,342, and a continuation-in-part of application No. PCT/US99/27438, filed on Nov. 19, 1999.

(60) Provisional application No. 60/130,560, filed on Apr. 22, 1999, provisional application No. 60/122,620, filed on Mar. 3, 1999, provisional application No. 60/119,386, filed on Feb. 10, 1999, and provisional application No. 60/109,401, filed on Nov. 20, 1998.

(51) Int. Cl.[7] ................................................. C12N 1/20

(52) U.S. Cl. .................................................... 435/252.3

(58) Field of Search ...................................... 435/252.3

(56) References Cited

U.S. PATENT DOCUMENTS

| | | | |
|---|---|---|---|
| 4,916,138 A | 4/1990 | Ueda et al. ................... 514/294 |
| 5,605,793 A | 2/1997 | Stemmer ......................... 435/6 |
| 5,672,491 A | 9/1997 | Khosla et al. .................. 435/48 |
| 5,686,295 A | 11/1997 | Jaoua et al. ............. 435/252.3 |
| 5,712,146 A | 1/1998 | Khosla et al. ......... 435/252.35 |
| 5,783,431 A | * 7/1998 | Peterson et al. ......... 435/172.3 |
| 5,811,238 A | 9/1998 | Stemmer et al. ................ 435/6 |
| 5,824,513 A | 10/1998 | Katz et al. ..................... 435/76 |
| 5,830,721 A | 11/1998 | Stemmer et al. ......... 435/172.1 |
| 5,830,750 A | 11/1998 | Khosla et al. ......... 435/252.35 |
| 5,843,718 A | 12/1998 | Khosla et al. ............. 435/69.1 |
| 5,969,145 A | 10/1999 | Schinzer et al. ............. 548/110 |
| 6,022,731 A | 2/2000 | Khosla et al. ......... 435/252.35 |
| 6,033,883 A | 3/2000 | Barr et al. ................... 435/148 |
| 6,121,029 A | * 9/2000 | Schupp et al. .............. 435/183 |

FOREIGN PATENT DOCUMENTS

| | | |
|---|---|---|
| DE | 41 38 042 | 5/1993 |
| EP | 0423714 B1 | 6/1994 |
| EP | 0428169 B | 3/1995 |
| WO | WO 93/10121 | 5/1993 |
| WO | WO 97/02358 | 1/1997 |
| WO | WO 97/13845 | 4/1997 |
| WO | WO 97/19086 | 5/1997 |
| WO | WO 98/08849 | 3/1998 |
| WO | WO 98/22461 | 5/1998 |
| WO | WO 98/25929 | 6/1998 |
| WO | WO 98/27203 | 6/1998 |
| WO | WO 98/49315 | 11/1998 |

(List continued on next page.)

OTHER PUBLICATIONS

Paitan et al. The First Gene in the Biosynthesis of the Polyketide Antibiotic TA of Myxococcus xanthus Codes for a Unique PKS Module Coupled to a Peptide Synthetase. J. Molecular Biology (Feb., 1999) 286:465–474.*

Beyer et al., Metabolic diversity in myxobacteria: identification of the myxalamid and the stigmatellin biosynthetic gene cluster of Stigmatella aurantiaca Sg a15 and (see continuation below) a combined polyketide–(poly)peptide gene cluster from the epothilone producing strain *Sorangium cellulosum* Sso ce90. Biochimica et Biophysica Acta (1999) 1445:185–195).*

(List continued on next page.)

*Primary Examiner*—Ponnathapu Achutamurthy
*Assistant Examiner*—Kathleen Kerr
(74) *Attorney, Agent, or Firm*—Kate H. Murashige; Morrison & Foerster LLP; Kevin Kaster, Esq.

(57) ABSTRACT

Recombinant Myxococcus host cell containing recombinant expression vectors containing epothilone polyketide synthase genes can produce epothilones C and D.

6 Claims, 4 Drawing Sheets

FOREIGN PATENT DOCUMENTS

| WO | WO 99/01124 | 1/1999 |
|---|---|---|
| WO | WO 99/02514 | 1/1999 |
| WO | WO 99/02669 | 1/1999 |
| WO | WO 99/03986 | 1/1999 |
| WO | WO 99/07692 | 2/1999 |
| WO | WO 99/43320 | 2/1999 |
| WO | WO 99/27890 | 6/1999 |
| WO | WO 99/39694 | 8/1999 |
| WO | WO 99/40047 | 8/1999 |
| WO | WO 99/42602 | 8/1999 |
| WO | WO 99/43653 | 9/1999 |
| WO | WO 99/54318 | 10/1999 |
| WO | WO 99/54319 | 10/1999 |
| WO | WO 99/54330 | 10/1999 |
| WO | WO 99/65913 | 12/1999 |
| WO | WO 99/66028 | 12/1999 |
| WO | WO 99/67252 | 12/1999 |
| WO | WO 99/67253 | 12/1999 |
| WO | WO 00/00485 | 1/2000 |
| WO | WO 00/01838 | 1/2000 |
| WO | WO 00 22139 A | 4/2000 |

OTHER PUBLICATIONS

Varon et al., "Mutation and Mapping of Genes Involved in Production of the Antibiotic TA in *Xyxococcus xanthus*." Antimicrobial Agents and Chemotherapy (1992) 36(10):2316–2321.
Oliynyk et al., "A Hybrid Modular Polyketide Synthase Obtained by Domain Swapping." Chemistry & Biology (1996) 3:833–839.
Balog D., et al. (1996). *Angew Chem Int Ed Engl* 35 (23/24):2801–2803.
Balog, D. et al. (1998). *Angew Chem Int Ed Engl* 37 (19):2675–2678.
Betlach, et al. (1998). *Biochem* 37:14937.
Bierman, et al. (1992). *Gene* 116:43–49.
Bollag, D. et al. (1995). *Cancer Res* 55:2325–2333.
Campos ans Zusman, (1975). *Proc Natl Acad Sci USA* 72:518–522.
Campos, et al. (1978). *J Mol Biol* 119:167–168.
Caspers, et al.(1994). *Cellular and Molecular Biology* 40(5):635–644.
Chou, T.C. et al. (1998). *Natl Acad Sci USA* 95 (16):9642–9647.
Gerth, K. et al. (1996). *J Antibiotics* 49:560–563.
Hahn D., et al.. (1991). *J. Bact* 173:5573–5577.
Hodgkin and Kaiser. (1979). *Mol Gen Genet* 171:177–191.
Hofle, et al. (1996). *Angew Chem Int Ed Engl* 35(13/14):1567–1569.
Kafeshi, et al. (1995). *Mol Microbiol* 15:483–494.
Kaiser, (1979). *Proc. Natl Acad Sci USA* 76:5952–5956.
Katz, et al. (1983), *J. Gen Microbiol* 129:2703–2714.
Keiser and Melton, (1988), *Gene* 65:83–91.
Lydiate, et al. (1985). *Gene* 35:223–235.
Magrini, et al. (1999). *J Bact* 181 (13):4062–4070.
Meng, et al. (1997). *JACS* 119 (42):10073–10092.
Molnar, I. et al. (2000), *Chemistry & Biology* 7 (2):97–109.
Muth, et al. (1989). *Mol Gen Genet* 219:341–348.
Salmi, et al. (1998). *J Bact* 180 (3):614–621.
Scholz, et al. (1989). *Gene* 75:271–278.
Servin–Gonzales, (1993). *Plasmid* 30:131–140.
Sheng, et al. (1995). *Nucleic Acids Res* 23:1990–1996.
Smokvina, et al. (1990). *Gene* 94:53–59.
Stassi, et al. (1998). *Appl Micribiol Biotechnol* 49:725–731.
Su, et al. (1997). *Angew Chem Int Ed Engl* 36 (19): 2093–2096.
Su, et al. (1997). *Angew Chem Int Ed Engl* 36 (7):757–759.
Tang, L. et al. (2000). *Science* 287:640–642.
Thompson, et al. (1982). *Gene* 20:51–62.
Vara, et al. (1989). *J Bacteriol* 171:5782–5791.
Witkowski, et al. (1999). *Biochem* 38(36): 11643–11650.
Wu and Kaiser. (1997). *J Bact* 179 (24):7748–7758.
An, J. and Kim, Y. (1998). *Eur J Biochem* 274(52):395–402.
Hamilton, C. et al. (1989). *J Bact* 171(9):4617–4622.
Hondo, T. et al. (1987). *Transplantation Proceedings* XIX(5) Suppl 6:17–22.
Jaoua, S. et al. (1992). *Plasmid* 28:157–165.
Link, A. et al. (1997). *J Bact* 179(20):6228–6237.
Silakowski, B. et al. (1999). *J Biol Chem* 274(52):37391–37399.
Strong, S. et al. (1997). *Nucleic Acids Res* 19:3959–3961.
Ueki, T. et al. (1996). *Gene* 183:153–157.

* cited by examiner

R =

X = CH$_2$, O, S
Y = CH$_2$, O, S

X = H, Me, Et, CH$_2$OH, Br
Y = O, S

X = H, Me, Et, Br, OH
Y = NH, O, S

X = NO$_2$, CN, Me, O-alkyl, halo, etc.
Y = CH, N

X = NO$_2$, CN, alkyl, aryl, halo, O-alkyl, etc.
Y = CH, N

X = NO$_2$, CN, alkyl, aryl, halo, O-alkyl, etc.
Y = CH, N

X = CH, N
Y = CH, N

X = CH$_2$, O, S, NH, N-alkyl, N-aryl
Y = CH$_2$, O, S, NH, N-alkyl, N-aryl

X = CH$_2$, O, S, NH, N-alkyl, N-aryl
Y = CH$_2$, O, S, NH, N-alkyl, N-aryl

MYXOCOCCUS HOST CELLS FOR THE PRODUCTION OF EPOTHILONES

CROSS-REFERENCE TO RELATED APPLICATIONS

This application is a CIP of U.S. patent application Ser. No. 09/443,501, filed Nov. 19, 1999, now issued as U.S. Pat. No. 6,303,342; and a CIP of PCT patent application US99/27438, filed Nov. 19, 1999; and claims benefit of U.S. provisional application Ser. Nos. 60/130,560, filed Apr. 22, 1999; 60/122,620, filed Mar. 3, 1999; 60/119,386, filed Feb. 10, 1999; and No. 60/109,401, filed Nov. 20, 1998, each of which is incorporated herein by reference.

REFERENCE TO GOVERNMENT FUNDING

This invention was supported in part by SBIR grant 1R43-CA79228-01. The U.S. government has certain rights in this invention.

FIELD OF THE INVENTION

The present invention provides recombinant methods and materials for producing polyketides in recombinant host cells. The recombinant host cells are from the suborder Cystobacterineae, preferably from the genera Myxococcus and Stigmatella that have been transformed with recombinant DNA expression vectors of the invention that encode modular or iterative polyketide synthase (PKS) genes. The recombinant host cells produce known and novel polyketides, including but not limited to epothilone and epothilone derivatives. The invention relates to the fields of agriculture, chemistry, medicinal chemistry, medicine, molecular biology, and pharmacology.

BACKGROUND OF THE INVENTION

Polyketides constitute a class of structurally diverse compounds synthesized, at least in part, from two carbon unit building block compounds through a series of Claisen type condensations and subsequent modifications. Polyketides include antibiotics such as tetracycline and erythromycin, anticancer agents such as epothilone and daunomycin, and immunosuppressants such as FK506 and rapamycin. Polyketides occur naturally in many types of organisms, including fungi and mycelial bacteria. Polyketides are synthesized in vivo by polyketides synthase enzymes commonly referred to as PKS enzymes. Two major types of PKS are known that differ in their structure and the manner in which they synthesize polyketides. These two types are commonly referred to as Type I or modular and Type II or iterative (aromatic) PKS enzymes.

The present invention provides methods and recombinant expression vectors and host cells for the production of modular or iterative PKS enzymes and the polyketides produced by those enzymes. Modular PKS enzymes are typically multi-protein complexes in which each protein contains multiple active sites, each of which is used only once during carbon chain assembly and modification. Iterative PKS enzymes are typically multi-protein complexes in which each protein contains only one or at most two active sites, each of which is used multiple times during carbon chain assembly and modification. As described in more detail below, a large number of the genes for both modular and aromatic PKS enzymes have been cloned.

Modular PKS genes are composed of coding sequences organized to encode a loading module, a number of extender modules, and a releasing domain. As described more fully below, each of these domains and modules corresponds to a polypeptide with one or more specific functions. Generally, the loading module is responsible for binding the first building block used to synthesize the polyketide and transferring it to the first extender module. The building blocks used to form complex polyketides are typically acylthioesters, most commonly acetyl, propionyl, malonyl, methylmalonyl, hydroxymalonyl, methoxymalonyl, and ethylmalonyl CoA. Other building blocks include amino acid-like acylthioesters. PKSs catalyze the biosynthesis of polyketides through repeated, decarboxylative Claisen condensations between the acylthioester building blocks. Each module is responsible for binding a building block, performing one or more functions on that building block, and transferring the resulting compound to the next module. The next module, in turn, is responsible for attaching the next building block and transferring the growing compound to the next module until synthesis is complete. At that point, the releasing domain, often an enzymatic thioesterase (TE) activity, cleaves the polyketide from the PKS.

The polyketide known as 6-deoxyerythronolide B (6-dEB) is synthesized by a prototypical modular PKS enzyme. The genes, known as eryAI, eryAII, and eryAIII, that code for the multi-subunit protein known as deoxyerythronolide B synthase or DEBS (each subunit is known as DEBS1, DEBS2, or DEBS3) that synthesizes 6-dEB are described in U.S. Pat. Nos. 5,712,146 and 5,824,513, incorporated herein by reference.

The loading module of the DEBS PKS consists of an acyltransferase (AT) and an acyl carrier protein (ACP). The AT of the DEBS loading module recognizes propionyl CoA (other loading module ATs can recognize other acyl-CoAs, such as acetyl, malonyl, methylmalonyl, or butyryl CoA) and transfers it as a thioester to the ACP of the loading module. Concurrently, the AT on each of the six extender modules of DEBS recognizes a methylmalonyl CoA (other extender module ATs can recognize other CoAs, such as malonyl or alpha-substituted malonyl CoAs, i.e., malonyl, ethylmalonyl, and 2-hydroxymalonyl CoA) and transfers it to the ACP of that module to form a thioester. Once DEBS is primed with acyl- and methylmalonyl-ACPs, the acyl group of the loading module migrates to form a thioester (trans-esterification) at the KS of the first extender module; at this stage, module one possesses an acyl-KS adjacent to a methylmalonyl ACP. The acyl group derived from the DEBS loading module is then covalently attached to the alpha-carbon of the extender group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module of DEBS, and the process continues.

The polyketide chain, growing by two carbons for each module of DEBS, is sequentially passed as a covalently bound thioester from module to module, in an assembly line-like process. The carbon chain produced by this process alone would possess a ketone at every other carbon atom, producing a polyketone, from which the name polyketide arises. Commonly, however, additional enzymatic activities modify the beta keto group of each two carbon unit just after it has been added to the growing polyketide chain but before it is transferred to the next module. Thus, in addition to the minimal module containing KS, AT, and ACP necessary to form the carbon-carbon bond, modules may contain a ketoreductase (KR) that reduces the keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. The DEBS modules include those with only a KR domain, only an inactive KR domain, and with all three KR, DH, and ER domains.

Once a polyketide chain traverses the final module of a PKS, it encounters the releasing domain, typically a thioesterase, found at the carboxyl end of most modular PKS enzymes. Here, the polyketide is cleaved from the enzyme and, for many but not all polyketides, cyclized. The polyketide can be modified further by tailoring or modification enzymes; these enzymes add carbohydrate groups or methyl groups, or make other modifications, i.e., oxidation or reduction, on the polyketide core molecule. For example, 6-dEB is hydroxylated, methylated, and glycosylated (glycosidated) to yield the well known antibiotic erythromycin A in the *Saccharopolyspora erythraea* cells in which it is produced naturally.

While the above description applies generally to modular PKS enzymes and specifically to DEBS, there are a number of variations that exist in nature. For example, many PKS enzymes comprise loading modules that, unlike the loading module of DEBS, comprise an "inactive" KS domain that functions as a decarboxylase. This inactive KS is in most instances called $KS^Q$, where the superscript is the single-letter abbreviation for the amino acid (glutamine) that is present instead of the active site cysteine required for ketosynthase activity. The epothilone PKS loading module contains a $KS^Y$ domain in which tyrosine has replaced the cysteine. Moreover, the synthesis of other polyketides begins with starter units that are unlike those bound by the DEBS or epothilone loading modules. The enzymes that bind such starter units can include, for example, an AMP ligase such as that employed in the biosynthesis of FK520, FK506, and rapamycin, a non-ribosomal peptide synthase (NRPS) such as that employed in the biosynthesis of leinamycin, or a soluble CoA ligase.

Other important variations in PKS enzymes relate to the types of building blocks incorporated as extender units. As for starter units, some PKS enzymes incorporate amino acid like acylthioester building blocks using one or more NRPS modules as extender modules. The epothilone PKS, for example, contains an NRPS module. Another such variation is found in the FK506, FK520, and rapamycin PKS enzymes, which contain an NRPS that incorporates a pipecolate residue and also serves as the releasing domain of the PKS. Yet another variation relates to additional activities in an extender module. For example, one module of the epothilone PKS contains a methyltransferase (MT) domain, which incorporates a methyl group into the polyketide.

Recombinant methods for manipulating modular and iterative PKS genes that take advantage of the organization of those genes and the multiple enzymatic activities they encode are described in U.S. Pat. Nos. 5,672,491; 5,712,146; 5,830,750; and 5,843,718; and in PCT patent publication Nos. 98/49315 and 97/02358, each of which is incorporated herein by reference. These and other patents describe recombinant expression vectors for the heterologous production of polyketides as well as recombinant PKS genes assembled by combining parts of two or more different PKS genes that produce novel polyketides. To date, such methods have been used to produce known or novel polyketides in organisms such as Streptomyces, which naturally produce polyketides, and *E. coli* and yeast, which do not naturally produce polyketides (see U.S. Pat. No. 6,033,883, incorporated herein by reference). In the latter hosts, polyketide production is dependent on the heterologous expression of a phosphopantetheinyl transferase, which activates the ACP domains of the PKS (see PCT publication No. 97/13845, incorporated herein by reference).

While such methods are valuable and highly useful, certain polyketides are expressed only at very low levels or are toxic to the heterologous host cell employed. As an example, the anticancer agent epothilone was produced in Streptomyces by heterologous expression of the epothilone PKS genes (Tang et al., Jan. 28, 2000, Cloning and heterologous expression of the epothilone gene cluster, Science, 287: 640–642, and U.S. patent application Ser. No. 09/443,501, filed Nov. 19, 1999, each of which is incorporated herein by reference). However, the production of epothilone was only about 50 to 100 µg/L and appeared to have a deleterious effect on the producer cells.

The epothilones were first identified as an antifungal activity extracted from the myxobacterium *Sorangium cellulosum* (see K. Gerth et al., 1996, *J. Antibiotics* 49: 560–563 and Germany Patent No. DE 41 38 042, each of which is incorporated herein by reference) and later found to have activity in a tubulin polymerization assay (see Bollag et al., 1995, *Cancer Res.* 55:2325–2333, incorporated herein by reference). The epothilones have since been extensively studied as potential antitumor agents for the treatment of cancer. The chemical structure of the epothilones produced by *Sorangium cellulosum* strain So ce 90 was described in Hofle et al., 1996, Epothilone A and B-novel 16-membered macrolides with cytotoxic activity: isolation, crystal structure, and conformation in solution, *Angew. Chem. Int. Ed. Engl.* 35(13/14): 1567–1569, incorporated herein by reference. The strain was found to produce two epothilone compounds, designated A (R=H) and B (R=CH$_3$), as shown below, which showed broad cytotoxic activity against eukaryotic cells and noticeable activity and selectivity against breast and colon tumor cell lines.

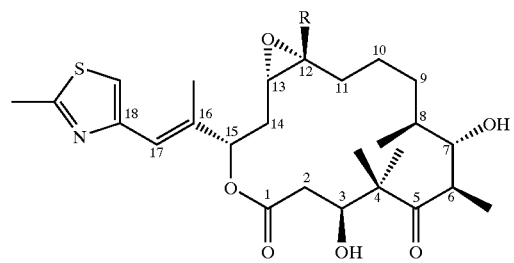

The desoxy counterparts of epothilones A and B, also known as epothilones C (R=H) and D (R=CH$_3$), are known to be less cytotoxic, and the structures of these epothilones are shown below.

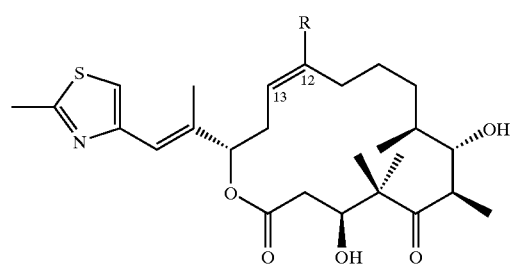

Two other naturally occurring epothilones have been described. These are epothilones E and F, in which the methyl side chain of the thiazole moiety of epothilones A and B has been hydroxylated to yield epothilones E and F, respectively.

Because of the potential for use of the epothilones as anticancer agents, and because of the low levels of epothilone produced by the native So ce 90 strain, a number of research teams undertook the effort to synthesize the epothilones. This effort has been successful (see Balog et al., 1996, Total synthesis of (−)-epothilone A, *Angew. Chem. Int. Ed. Engl.* 35(23/24): 2801–2803; Su et al., 1997, Total synthesis of (−)-epothilone B: an extension of the Suzuki coupling method and insights into structure-activity relationships of the epothilones, *Angew. Chem. Int. Ed. Engl.* 36(7): 757–759; Meng et al., 1997, Total syntheses of epothilones A and B, *JACS* 119(42): 10073–10092; and Balog et al., 1998, A novel aldol condensation with 2-methyl-4-pentenal and its application to an improved total synthesis of epothilone B, *Angew. Chem. Int. Ed. Engl.* 37(19): 2675–2678, each of which is incorporated herein by reference). Despite the success of these efforts, the chemical synthesis of the epothilones is tedious, time-consuming, and expensive. Indeed, the methods have been characterized as impractical for the full-scale pharmaceutical development of an epothilone.

A number of epothilone derivatives, as well as epothilones A-D, have been studied in vitro and in vivo (see Su et al., 1997, Structure-activity relationships of the epothilones and the first in vivo comparison with paclitaxel, *Angew. Chem. Int. Ed. Engl.* 36(19): 2093–2096; and Chou et al., Aug. 1998, Desoxyepothilone B: an efficacious microtubule-targeted antitumor agent with a promising in vivo profile relative to epothilone B, *Proc. Natl. Acad. Sci. USA* 95: 9642–9647, each of which is incorporated herein by reference). Additional epothilone derivatives and methods for synthesizing epothilones and epothilone derivatives are described in PCT patent publication Nos. 00/00485, 99/67253, 99/67252, 99/65913, 99/54330, 99/54319, 99/54318, 99/43653, 99/43320, 99/42602, 99/40047, 99/27890, 99/07692, 99/02514, 99/01124, 98/25929, 98/22461, 98/08849, and 97/19086; U.S. Pat. No. 5,969,145; and Germany patent publication No. DE 41 38 042, each of which is incorporated herein by reference.

There remains a need for economical means to produce not only the naturally occurring epothilones but also the derivatives or precursors thereof, as well as new epothilone derivatives with improved properties. There remains a need for a host cell that produces epothilones or epothilone derivatives that is easier to manipulate and ferment than the natural producer *Sorangium cellulosum* yet produces more of the desired polyketide product. The present invention meets these by providing host cells that produce polyketides at high levels and are useful in the production of not only epothilones, including new epothilone derivatives described herein, but also other polyketides.

SUMMARY OF THE INVENTION

In one embodiment, the present invention provides recombinant host cells of the suborder Cystobacterineae containing recombinant expression vectors that encode heterologous PKS genes and produce polyketides synthesized by the PKS enzymes encoded on those vectors. In a preferred embodiment, the host cells are from the genus Myxococcus or the genus Stigmatella. In especially preferred embodiments, the host cells are selected from the group consisting of *M. stipitatus, M. fulvus, M. xanthus, M. virescens, S. erecta*, and *S. aurantiaca*.

In another embodiment, the present invention provides recombinant DNA vectors capable of chromosomal integration or extrachromosomal replication in the host cells of the invention. The vectors of the invention comprise at least a portion of a PKS coding sequence and are capable of directing expression of a functional PKS enzyme in the host cells of the invention.

In another embodiment, the present invention provides a method for producing a polyketide in a host cell of the suborder Cystobacterineae, which polyketide is not naturally produced in said host cell, said method comprising culturing the host cell transformed with a recombinant DNA vector of the invention under conditions such that a PKS gene encoded on the vector is expressed and said polyketide is produced.

In a preferred embodiment, the recombinant host cell of the invention produces epothilone or an epothilone derivative. Thus, the present invention provides recombinant host cells that produce a desired epothilone or epothilone derivative. In a preferred embodiment, the host cell produces the epothilones at equal to or greater than 10 mg/L. In one embodiment, the invention provides host cells that produce one or more of the epothilones or epothilone derivatives at higher levels than produced in the naturally occurring organisms that produce epothilones. In another embodiment, the invention provides host cells that produce mixtures of epothilones that are less complex than the mixtures produced by naturally occurring host cells that produce epothilones.

In an especially preferred embodiment, the host cells of the invention produce less complex mixtures of epothilones than do naturally occurring cells that produce epothilones. Naturally occurring cells that produce epothilones typically produce a mixture of epothilones A, B, C, D, E, and F. The table below summarizes the epothilones produced in different illustratrive host cells of the invention.

| Cell Type | Epothilones Produced | Epothilones Not Produced |
|---|---|---|
| 1 | A, B, C, D | E, F |
| 2 | A, C | B, D, E, F |
| 3 | B, D | A, C, E, F |
| 4 | B | A, C, D, E, F |
| 5 | D | A, B, C, E, F |

Thus, the recombinant host cells of the invention also include host cells that produce only one desired epothilone or epothilone derivative.

In a related preferred embodiment, the invention provides recombinant DNA expression vectors that encode all or a portion of the epothilone PKS. Thus, the present invention provides recombinant DNA expression vectors that encode the proteins required to produce epothilones A, B, C, and D in the host cells of the invention. The present invention also provides recombinant DNA expression vectors that encode portions of these proteins. The present invention also provides recombinant DNA compounds that encode a hybrid protein, which hybrid protein includes all or a portion of a protein involved in epothilone biosynthesis and all or a portion of a protein involved in the biosynthesis of another polyketide or non-ribosomal-derived peptide.

In another embodiment, the present invention provides novel epothilone derivative compounds in substantially pure form useful in agriculture, veterinary practice, and medicine. In one embodiment, the compounds are useful as fungicides. In another embodiment, the compounds are useful in cancer chemotherapy. In a preferred embodiment, the compound is an epothilone derivative that is at least as potent against tumor cells as epothilone B or D. In another embodiment, the compounds are useful as immunosuppressants. In another embodiment, the compounds are useful in the manufacture of another compound. In a preferred embodiment, the compounds are formulated in a mixture or solution for administration to a human or animal.

In another embodiment, the present invention provides a method of treating cancer, which method comprises administering a therapeutically effective amount of a novel epothilone compound of the invention.

These and other embodiments of the invention are described in more detail in the following description, the examples, and claims set forth below.

DETAILED DESCRIPTION OF THE INVENTION

Figure 1:
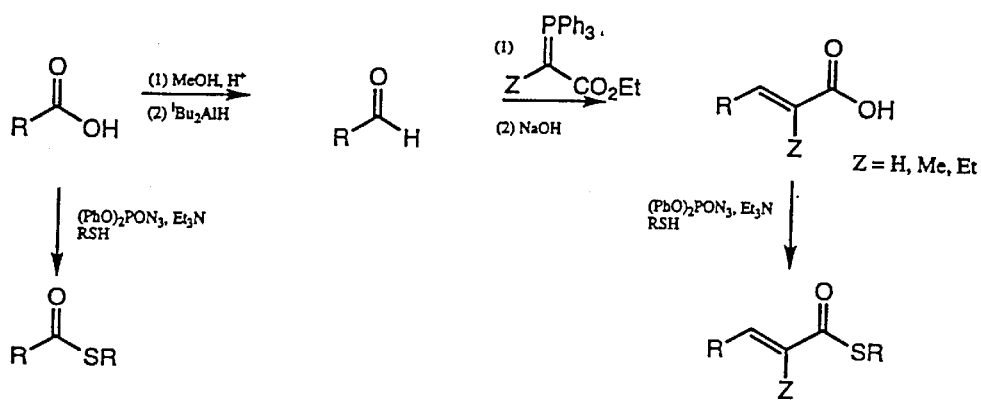
FIG. 1 shows a number of precursor compounds to N-acetyl cysteamine thioester derivatives that can be supplied to an epothilone PKS of the invention in which the NRPS-like module one or module 2 KS domain has been inactivated to produce a novel epothilone derivative. A general synthetic procedure for making such compounds is also shown.
Figure 1:
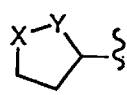
Figure 1:
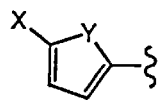
Figure 1:
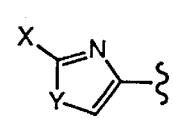
Figure 1:
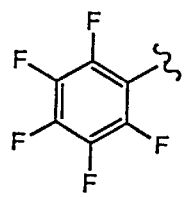
Figure 1:
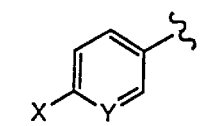
Figure 1:
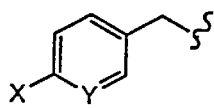
Figure 1:
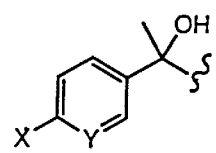
Figure 1:
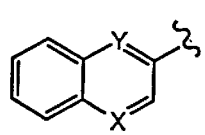
Figure 1:
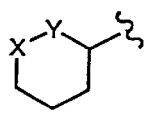
Figure 1:
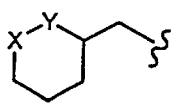

In one embodiment, the present invention provides recombinant host cells of the suborder Cystobacterineae containing recombinant expression vectors that encode heterologous PKS genes and produce polyketides synthesized by the PKS enzymes encoded on those vectors. As used herein, the term recombinant refers to a compound or composition produced by human intervention, typically by specific and directed manipulation of a gene or portion thereof. The suborder Cystobacterineae is one of two (the other is Sorangineae, which includes the epothilone producer *Sorangium cellulosum*) in the order Myxococcales. The suborder Cystobacterineae includes the family Myxococcaceae and the family Cystobacteraceae. The family Myxococcaceae includes the genus Angiococcus (i.e., A. disciforrmis), the genus Myxococcus, and the genus Corallococcus (i.e., *C. macrosporus, C. corralloides,* and *C. exiguus*). The family Cystobacteraceae includes the genus Cystobacter (i.e., *C. fuscus, C. ferrugineus, C. minor, C. velatus,* and *C. violaceus*), the genus Melittangium (i.e., *M. boletus* and *M. lichenicola*), the genus Stigmatella (i.e., *S. erecta* and *S. aurantiaca*), and the genus Archangium (i.e., *A. gephyra*). Especially preferred host cells of the invention are those that produce a polyketide at equal to or greater than 10 to 20 mg/L, more preferably at equal to or greater than 100 to 200 mg/L, and most preferably at equal to or greater than 1 to 2 g/L.

In a preferred embodiment, the host cells of the invention are from the genus Myxococcus or the genus Stigmatella. In especially preferred embodiments, the host cells are selected from the group consisting of *M. stipitatus, M. fulvus, M. xanthus, M. virescens, S. erecta,* and *S. aurantiaca*. Especially preferred Myxococcus host cells of the invention are those that produce a polyketide at equal to or greater than 10 to 20 mg/L, more preferably at equal to or greater than 100 to 200 mg/L, and most preferably at equal to or greater than 1 to 2 g/L. Especially preferred are *M. xanthus* host cells that produce at these levels. *M. xanthus* host cells that can be employed for purposes of the invention include the DZ1 cell line (Campos et al., 1978, *J. Mol. Biol.* 119: 167–178, incorporated herein by reference), the TA-producing cell line ATCC 31046, the DK1219 cell line (Hodgkin and Kaiser, 1979, *Mol. Gen. Genet.* 171: 177–191, incorporated herein by reference), and the DK1622 cell line (Kaiser, 1979, *Proc. Natl. Acad. Sci. USA* 76: 5952–5956, incorporated herein by reference).

The host cells of the invention comprise a recombinant DNA expression vector, and in another embodiment, the present invention provides recombinant DNA vectors capable of chromosomal integration or extrachromosomal replication in these host cells. The vectors of the invention comprise at least a portion of a PKS coding sequence and are capable of directing expression of a functional PKS enzyme in the host cells of the invention. As used herein, the term expression vector refers to any nucleic acid that can be introduced into a host cell. An expression vector can be maintained stably or transiently in a cell, whether as part of the chromosomal or other DNA in the cell or in any cellular compartment, such as a replicating vector in the cytoplasm. An expression vector also comprises a gene that serves to direct the synthesis RNA that is translated into a polypeptide in the cell or cell extract. Thus, the vector either includes a promoter to enhance gene expression or is integrated into a site in the chromosome such that gene expression is obtained. Furthermore, expression vectors typically contain additional functional elements, such as resistance-conferring genes to act as selectable markers and regulatory genes to enhance promoter activity.

Typically, the expression vector will comprise one or more marker genes by which host cells containing the vector can be identified and/or selected. Illustrative antibiotic resistance conferring genes for use in vectors of the invention include the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes. Selectable markers for use in *Myxococcus xanthus* include kanamycin, tetracycline, chloramphenicol, zeocin, spectinomycin, and streptomycin resistance conferring genes.

The various components of an expression vector can vary widely, depending on the intended use of the vector. In particular, the components depend on the host cell(s) in which the vector will be used and the manner in which it is intended to function. For example, certain preferred vectors of the invention are integrating vectors: the vectors integrate into the chromosomal DNA of the host cell. Such vectors can comprise a phage attachment site or DNA segments complementary to segments of the host cell chromosomal DNA to direct integration. Moreover, and as exemplified herein, a series of such vectors can be used to build the PKS gene cluster in the host cell, with each vector comprising only a portion of the complete PKS gene cluster. Thus, the recombinant DNA expression vectors of the invention may comprise only a portion of a PKS gene. Homologous recombination can also be used to delete, disrupt, or alter a gene, including a heterologous PKS gene previously introduced into the host cell.

In a preferred embodiment, the present invention provides expression vectors and recombinant Myxococcus, preferably *M. xanthus,* host cells containing those expression vectors that produce a polyketide. Presently, vectors that replicate extrachromosomally in *M. xanthus* are not known. There are, however, a number of phage known to integrate into *M. xanthus* chromosomal DNA, including Mx8, Mx9, Mx81, and Mx82. The integration and attachment functions of these phages can be placed on plasmids to create phage-based expression vectors that integrate into the *M. xanthus* chromosomal DNA. Of these, phage Mx9 and Mx8 are preferred for purposes of the present invention. Plasmid pPLH343, described in Salmi et al., Feb. 1998, Genetic determinants of immunity and integration of temperate *Myxococcus xanthus* phage Mx8, *J. Bact.* 180(3): 614–621, is a plasmid that replicates in *E. coli* and comprises the phage Mx8 genes that encode the attachment and integration functions.

A wide variety of promoters are available for use in the preferred Myxococcus expression vectors of the invention. See Example 8, below. For example, the promoter of the epothilone PKS gene (see U.S. patent application Ser. No. 09/443,501, filed Nov. 19, 1999, incorporated herein by reference) functions in *M. xanthus* host cells. The promoter can be used to drive expression of one or more epothilone PKS genes or another PKS gene product in recombinant host cells. Another preferred promoter for use in *Myxococcus xanthus* host cells for purposes of expressing a recombinant PKS of the invention is the promoter of the pilA gene of *M. xanthus*. This promoter, as well as two *M. xanthus* strains that express high levels of gene products from genes controlled by the pilA promoter, a pilA deletion strain and a pilS deletion strain, are described in Wu and Kaiser, Dec. 1997, Regulation of expression of the pilA gene in *Myxococcus xanthus, J. Bact.* 179(24):7748–7758, incorporated herein by reference. The invention present invention also provides recombinant Myxococcus host cells comprising both the pilA and pilS deletions. Another preferred promoter is the starvation dependent promoter of the sdck gene.

Figure 2:
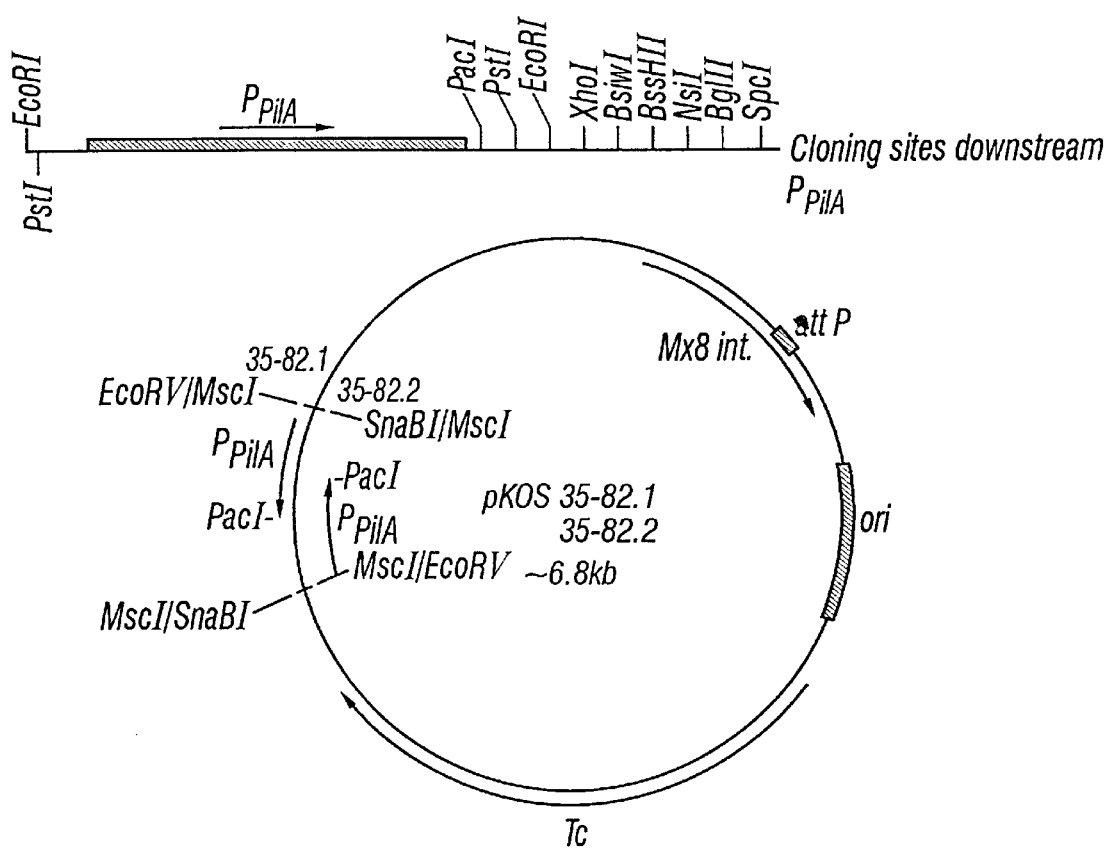
FIG. 2 shows restriction site and function maps of plasmids pKOS35-82.1 and pKOS35-82.2.

The present invention provides preferred expression vectors for use in preparing the recombinant *Myxococcus xanthus* expression vectors and host cells of the invention. These vectors, designated plasmids pKOS35-82.1 and pKOS35-82.2 (FIG. 2), are able to replicate in *E. coli* host cells as well as integrate into the chromosomal DNA of *M. xanthus*. The vectors comprise the Mx8 attachment and integration genes as well as the pilA promoter with restriction enzyme recognition sites placed conveniently downstream. The two vectors differ from one another merely in the orientation of the pilA promoter on the vector and can be readily modified to include the epothilone PKS and modification enzyme genes of the invention. The construction of the vectors is described in Example 1.

In another embodiment, the present invention provides a method for producing a polyketide in a host cell of the suborder Cystobacterineae, which polyketide is not naturally produced in said host cell, said method comprising culturing the host cell transformed with a recombinant DNA vector of the invention under conditions such that a PKS gene encoded on the vector is expressed and said polyketide is produced. With this method, any of the diverse members of the polyketides produced by modular PKS enzymes can be prepared. In addition, novel polyketides derived from hybrid or other recombinant PKS genes can also be prepared using this method. In a preferred embodiment, the PKS genes encode a modular PKS.

A large number of modular PKS genes have been cloned and are immediately available for use in the vectors and methods of the invention. The polyketides produced by PKS enzymes are often further modified by polyketide modification enzymes, called tailoring enzymes, that hydroxylate, epoxidate, methylate, and glycosylate the polyketide product of the PKS. In accordance with the methods of the invention, these genes can also be introduced into the host cell to prepare a modified polyketide of interest. The following Table lists references describing illustrative PKS genes and to corresponding enzymes that can be utilized in the construction of the recombinant PKSs and the corresponding DNA compounds that encode them of the invention. Also presented are various references describing polyketide tailoring and modification enzymes and corresponding genes that can be employed to make the recombinant DNA compounds of the present invention.

PKS and Polyketide Tailoring Enzyme Genes
Avermectin
U.S. Pat. Nos. 5,252,474; 4,703,009; and EP Pub. No. 118,367 to Merck. MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, *Gene* 115: 119–125, Complex Organization of the *Streptomyces avermitilis* genes encoding the avermectin polyketide synthase.
Ikeda and Omura, 1997, *Chem. Res.* 97: 2599–2609, Avermectin biosynthesis.
Candicidin (FR008)
Hu et al., 1994, *Mol. Microbiol.* 14: 163–172.
Epothilone
PCT Pub. No. 99/66028 to Novartis.
PCT Pat. App. No. US99/27438 to Kosan.
Erythromycin
PCT Pub. No. 93/13663; U.S. Pat. Nos. 6,004,787; and 5,824,513 to Abbott.
Donadio et al., 1991, *Science* 252:675–9.
Cortes et al., Nov. 8, 1990, *Nature* 348:176–8, An unusually large multifunctional polypeptide in the erythromycin producing polyketide synthase of *Saccharopolyspora erythraea*.
Glycosylation Enzymes
PCT Pub. No. 97/23630 and U.S. Pat. No. 5,998,194 to Abbott.
FK-506
Motamedi et al., 1998, The biosynthetic gene cluster for the macrolactone ring of the immunosuppressant FK-506, *Eur. J. biochem.* 256: 528–534.
Motamedi et al., 1997, Structural organization of a multifunctional polyketide synthase involved in the biosynthesis of the macrolide immunosuppressant FK-506, *Eur. J. Biochem.* 244: 74–80.
Methyltransferase
U.S. Pat. No. 5,264,355 and U.S. Pat. No. 5,622,866 to Merck.
Motamedi et al., 1996, Characterization of methyltransferase and hydroxylase genes involved in the biosynthesis of the immunosuppressants FK-506 and FK-520, *J. Bacteriol.* 178: 5243–5248.
FK-520
PCT Pub. No. 00/20601 and U.S. patent application Ser. No. 09/410,551, filed Oct. 1, 1999 to Kosan.
Nielsen et al., 1991, *Biochem.* 30:5789–96.
Lovastatin
U.S. Pat. No. 5,744,350 to Merck.
Narbomycin
U.S. patent application Ser. No. 09/434,288, filed Nov. 5, 1999, now issued as U.S. Pat. No. 6,303,767, to Kosan.

Nemadectin
  MacNeil et al., 1993, *supra*.
Niddamycin
  PCT Pub. No. 98/51695 to Abbott.
  Kakavas et al., 1997, Identification and characterization of the niddamycin polyketide synthase genes from *Streptomyces caelestis*, *J. Bacteriol*. 179: 7515–7522.
Oleandomycin
  Swan et al., 1994, Characterisation of a Streptomyces antibioticus gene encoding a type I polyketide synthase which has an unusual coding sequence, *Mol. Gen. Genet.* 242: 358–362.
  U.S. patent application Ser. No. 09/144,085, filed Aug. 31, 1998, now issued as U.S. Pat. No. 6,280,999, to Kosan.
  Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.
  PCT Pat. App. Pub. No. WO 99/05283 to Hoechst.
Picromycin
  PCT Pub. No. 99/61599 to Kosan..
  PCT Pub. No. 00/00620 to the University of Minnesota.
  Xue et al., 1998, Hydroxylation of macrolactones YC-17 and narbomycin is mediated by the pikC-encoded cytochrome P450 in *Streptomyces venezuelae*, *Chemistry & Biology* 5(11): 661–667.
  Xue et al., Oct. 1998, A gene cluster for macrolide antibiotic biosynthesis in *Streptomyces venezuelae*: Architecture of metabolic diversity, *Proc. Natl. Acad. Sci. USA* 95:12111 12116.
Platenolide
  EP Pub. No. 791,656; and U.S. Pat. No. 5,945,320 to Lilly.
Rapamycin
  Schwecke et al., Aug. 1995, The biosynthetic gene cluster for the polyketide rapamycin, *Proc. Natl. Acad. Sci. USA* 92:7839–7843.
  Aparicio et al., 1996, Organization of the biosynthetic gene cluster for rapamycin in *Streptomyces hygroscopicus*: analysis of the enzymatic domains in the modular polyketide synthase, *Gene* 169: 9–16.
Rifamycin
  PCT Pub. No. WO 98/07868 to Novartis.
  August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.
Sorangium PKS
  U.S. patent application Ser. No. 09/144,085, filed Aug. 31, 1998 to Kosan.
Soraphen
  U.S. Pat. No. 5,716,849 to Novartis.
  Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spinocyn
  PCT Pub. No. 99/46387 to DowElanco.
Spiramycin
  U.S. Pat. No. 5,098,837 to Lilly.
  Activator Gene
  U.S. Pat. No. 5,514,544 to Lilly.
Tylosin
  U.S. Pat. Nos. 5,876,991; 5,672,497; 5,149,638; EP Pub. No. 791,655; and EP Pub. No. 238,323 to Lilly.
  Kuhstoss et al., 1996, *Gene* 183:231–6., Production of a novel polyketide through the construction of a hybrid polyketide synthase.
  Tailoring enzymes
  Merson-Davies and Cundliffe, 1994, *Mol. Microbiol.* 13: 349–355. Analysis of five tylosin biosynthetic genes from the tylBA region of the *Streptomyces fradiae* genome.

Any of the above genes, with or without the genes for polyketide modification, if any, can be employed in the recombinant DNA expression vectors of the invention. Moreover, the host cells of the invention can be constructed by transformation with multiple vectors, each containing a portion of the desired PKS and modification enzyme gene cluster; see U.S. Pat. No. 6,033,883, incorporated herein by reference.

For improved production of a polyketide in a host cell of the invention, including Myxococcus host cells, one can also transform the cell to express a heterologous phosphopantetheinyl transferase. PKS proteins require phosphopantetheinylation of the ACP domains of the loading and extender modules as well as of the PCP domain of any NRPS. Phosphopantetheinylation is mediated by enzymes called phosphopantetheinyl transferases (PPTases). To produce functional PKS enzyme in host cells that do not naturally express a PPTase able to act on the desired PKS enzyme or to increase amounts of functional PKS enzyme in host cells in which the PPTase is limiting, one can introduce a heterologous PPTase, including but not limited to Sfp, as described in PCT Pub. Nos. 97/13845 and 98/27203, and U.S. patent application Ser. No. 08/728,742, filed Oct. 11, 1996, and U.S. Pat. No. 6,033,883, each of which is incorporated herein by reference.

The host cells of the invention can be used not only to produce a polyketide found in nature but also to produce polyketides produced from recombinant PKS genes and modification enzymes. In one important embodiment, the present invention provides recombinant DNA expression vectors that comprise a hybrid PKS. For purposes of the present invention a hybrid PKS is a recombinant PKS that comprises all or part of one or more extender modules, loading module, and thioesterase/cyclase domain of a first PKS and all or part of one or more extender modules, loading module, and thioesterase/cyclase domain of a second PKS.

Those of skill in the art will recognize that all or part of either the first or second PKS in a hybrid PKS of the invention need not be isolated from a naturally occurring source. For example, only a small portion of an AT domain determines its specificity. See U.S. patent application Ser. No. 09/346,860, now issued as U.S. Pat. No. 6,221,641, and PCT Pub. No. 00/01838, each of which is incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

As the above Table illustrates, there are a wide variety of PKS genes that serve as readily available sources of DNA and sequence information for use in constructing the hybrid PKS-encoding DNA compounds of the invention. Methods for constructing hybrid PKS-encoding DNA compounds are described in U.S. Pat. Nos. 6,022,731; 5,672,491; and 5,712,146 and U.S. patent application Ser. No. 09/073,538, filed May 6, 1998, and Ser. No.09/141,908, filed Aug 28, 1998, each of which is incorporated herein by reference. The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Those of skill in the art will appreciate that a hybrid PKS of the invention includes but is not limited to a PKS of any of the following types: (i) a PKS that contains a module in which at least one of the domains is from a heterologous module; (ii) a PKS that contains a module from a heterologous PKS; (iii) a PKS that contains a protein from a heterologous PKS; and (iv) combinations of the foregoing.

Hybrid PKS enzymes of the invention are often constructed by replacing coding sequences for one or more domains of a module from a first PKS with coding sequences for one or more domains of a module from a second PKS to construct a recombinant coding sequence. Generally, any reference herein to inserting or replacing a KR, DH, and/or ER domain includes the replacement of the associated KR, DH, or ER domains in that module, typically with corresponding domains from the module from which the inserted or replacing domain is obtained. The KS and/or ACP of any module can also be replaced, if desired or beneficial, with another KS and/or ACP. In each of these replacements or insertions, the heterologous KS, AT, DH, KR, ER, or ACP coding sequence can originate from a coding sequence from another module of the same or different PKS or from chemical synthesis to obtain the hybrid PKS coding sequence.

While an important embodiment of the present invention relates to hybrid PKS genes, the present invention also provides recombinant PKS genes in which there is no second PKS gene sequence present but which differ from a naturally occurring PKS gene by one or more deletions. The deletions can encompass one or more modules or domains and/or can be limited to a deletion within one or more modules or domains. When a deletion encompasses an entire extender module (other than an NRPS module), the resulting polyketide derivative is at least two carbons shorter than the compound produced from the PKS from which the deleted version was derived. The deletion can also encompass an NRPS module and/or a loading module. When a deletion is within a module, the deletion typically encompasses a KR, DH, or ER domain, or both DH and ER domains, or both KR and DH domains, or all three KR, DH, and ER domains.

To construct any PKS of the invention, one can employ a technique, described in PCT Pub. No. 98/27203 and U.S. Pat. No. 6,033,883, each of which is incorporated herein by reference, in which the various genes of the PKS and optionally genes for one or more polyketide modification enzymes are divided into two or more, often three, segments, and each segment is placed on a separate expression vector (see also, U.S. patent application Ser. No. 09/548,060, filed Apr. 14, 2000, which claims priority to Ser. No. 60/129,731, filed Apr. 16, 1999, both of which are incorporated herein by reference). In this manner, the full complement of genes can be assembled and manipulated more readily for heterologous expression, and each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors. In this and other contexts, the genes encoding the desired PKS not only can be present on two or more vectors, but also can be ordered or arranged differently from that which exists in the native producer organism from which the genes were derived.

In a preferred and illustrative embodiment, the recombinant host cell of the invention produces epothilone or an epothilone derivative. The epothilones (epothilone A, B, C, D, E, and F) and compounds structurally related thereto (epothilone derivatives) are potent cytotoxic agents specific for eukaryotic cells. These compounds have application as anti-fungals, cancer chemotherapeutics, and immunosuppressants. The epothilones are produced at very low levels in the naturally occurring *Sorangium cellulosum* cells in which they have been identified. Moreover, *S. cellulosum* is very slow growing, and fermentation of *S. cellulosum* strains is difficult and time-consuming. One important benefit conferred by the present invention is the ability simply to produce an epothilone or epothilone derivative in a non-*S. cellulosum* host cell. Another advantage of the present invention is the ability to produce the epothilones at higher levels and in greater amounts in the recombinant host cells provided by the invention than possible in the naturally occurring epothilone producer cells. Yet another advantage is the ability to produce an epothilone derivative in a recombinant host cell. Thus, the present invention provides recombinant host cells that produce a desired epothilone or epothilone derivative. In a preferred embodiment, the host cell produces the epothilones at equal to or greater than 10 mg/L. In one embodiment, the invention provides host cells that produce one or more of the epothilones or epothilone derivatives at higher levels than produced in the naturally occurring organisms that produce epothilones. In another embodiment, the invention provides host cells that produce mixtures of epothilones that are less complex than the mixtures produced by naturally occurring host cells that produce epothilones.

In an especially preferred embodiment, the host cells of the invention produce less complex mixtures of epothilones than do naturally occurring cells that produce epothilones. Naturally occurring cells that produce epothilones typically produce a mixture of epothilones A, B, C, D, E, and F. The table below summarizes the epothilones produced in different illustratrive host cells of the invention.

| Cell Type | Epothilones Produced | Epothilones Not Produced |
| --- | --- | --- |
| 1 | A, B, C, D | E, F |
| 2 | A, C | B, D, E, F |
| 3 | B, D | A, C, E, F |
| 4 | B | A, C, D, E, F |
| 5 | D | A, B, C, E, F |

Thus, the recombinant host cells of the invention also include host cells that produce only one desired epothilone or epothilone derivative.

An analysis of the domains of the epothilone PKS suggests that the PKS enzyme catalyzes the production of epothilones G and H, which differ from one another in that epothilone G has a hydrogen at C-12 and epothilone H has a methyl group at that position. The variance at the C-12 position is predicted to arise from the ability of the corresponding AT domain (extender module 4) of the PKS to bind either malonyl CoA, leading to hydrogen, or methylmalonyl CoA, leading to methyl. However, epothilones G and H have not been observed in nature or in the recombinant host cells of the invention; instead, the products of the PKS appear to be epothilones C and D, which differ from epothilones G and H, respectively, by having a C-12 to C-13 double bond and lacking a C-13 hydroxyl substituent. Thus, the dehydration reaction that would form epothilones C and D from epothilones G and H may be carried out by the epothilone PKS itself or by another enzymatic activity that is present in the host cells in which the epothilones have been produced to date. Epothilones A and B are formed from epothilones C and D, respectively, by epoxidation of the C-12 to C-13 double bond by the epoK gene product. Epothilones E and F are formed from epothilones A and B, respectively, by hydroxylation of the C-21 methyl group.

Thus expression of the epothilone PKS genes and the epoK gene in a host cell of the invention leads to the production of epothilones A, B, C, and D. If the epoK gene is not present or is rendered inactive by mutation, then only epothilones C and D are produced. If the AT domain of extender module 4 is replaced by an AT domain specific for malonyl Co A, then epothilones A and C only are produced, and if there is no functional epoK gene, then only epothilone C is produced. If the AT domain of extender module 4 is replaced by an AT domain specific for methylmalonyl Co A, then epothilones B and D only are produced, and if there is no functional epoK gene, then only epothilone D is produced.

The epothilone PKS and modification enzyme genes were cloned from the epothilone producing strain, *Sorangium cellulosum* SMP44. Total DNA was prepared from this strain using the procedure described by Jaoua et al., 1992, *Plasmid* 28: 157–165, incorporated herein by reference. A cosmid library was prepared from *S. cellulosum* genomic DNA in pSupercos (Stratagene). The entire PKS and modification enzyme gene cluster was isolated in four overlapping cosmid clones (deposited with the American Type Culture Collection (ATCC), Manassas, Va., USA, and assigned ATCC accession numbers as follows pKOS35-70.1A2 (ATCC 203782), pKOS35-70.4 (ATCC 203781), pKOS35-70.8A3 (ATCC 203783), and pKOS35-79.85 (ATCC 203780)) and the DNA sequence determined, as set forth in U.S. patent application Ser. No. 09/443,501, filed Nov. 19, 1999, incorporated herein by reference. DNA sequence analysis revealed a PKS gene cluster with a loading module and nine extender modules. Downstream of the PKS sequence is an open reading frame (ORF), designated epoK, that shows strong homology to cytochrome P450 oxidase genes and encodes the epothilone epoxidase modification enzyme.

The PKS genes are organized in 6 ORFs. At the polypeptide level, the loading module and extender modules 1 (an NRPS), 2, and 9 appear on individual polypeptides; their corresponding genes are designated epoA, epoB, epoC and epoF respectively. Modules 3, 4, 5, and 6 are contained on a single polypeptide whose gene is designated epoD, and modules 7 and 8 are on another polypeptide whose gene is designated epoE. It is clear from the spacing between ORFs that epoC, epoD, epoE and epoF constitute an operon. The epoA, epoB, and epoK gene may be also part of the large operon, but there are spaces of approximately 100 bp between epoB and epoC and 115 bp between epoF and epoK which could contain a promoter. The epothilone PKS gene cluster is shown schematically below.

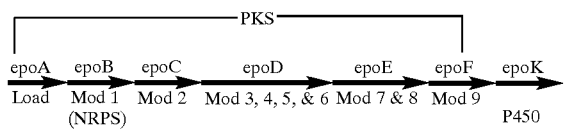

Immediately downstream of epoK, the P450 epoxidase gene, is ORF1, which encodes a polypeptide that appears to include membrane spanning domains and may be involved in epothilone transport. This ORF is followed by a number of ORFs that include genes that may encode proteins involved in transport and regulation.

A detailed examination of the modules shows an organization and composition consistent with one able to be used for the biosynthesis of epothilone. The description that follows is at the polypetide level. The sequence of the AT domain in the loading module and in extender modules 3, 4, 5, and 9 shows similarity to the consensus sequence for malonyl loading modules, consistent with the presence of an H side chain at C-14, C-12 (epothilones A and C), C-10, and C-2, respectively, as well as the loading module. The AT domains in modules 2, 6, 7, and 8 resemble the consensus sequence for methylmalonyl specifying AT domains, again consistent with the presence of methyl side chains at C-16, C-8, C-6, and C-4 respectively.

The loading module contains a KS domain in which the cysteine residue usually present at the active site is instead a tyrosine. This domain is designated as $KS^y$ and serves as a decarboxylase, which is part of its normal function, but cannot function as a condensing enzyme. Thus, the loading module is expected to load malonyl CoA, move it to the ACP, and decarboxylate it to yield the acetyl residue required for condensation with cysteine. Module 1 is the non-ribosomal peptide synthetase that activates cysteine and catalyzes the condensation with acetate on the loading module. The sequence contains segments highly similar to ATP-binding and ATPase domains, required for activation of amino acids, a phosphopantotheinylation site, and an elongation domain. Module 2 determines the structure of epothilone at C-15-C-17. The presence of the DH domain in module 2 yields the C-16-17 dehydro moiety in the molecule. The domains in module 3 are consistent with the structure of epothilone at C-14 and C-15; the OH that comes from the action of the KR is employed in the lactonization of the molecule. Module 4 controls the structure at C-12 and C-13 where a double bond is found in epothilones C and D. Although the sequence of the AT domain appears to resemble those that specify malonate loading, it can also load methylmalonate, thereby accounting in part for the mixture of epothilones found in the fermentation broths of the naturally producing organisms.

A significant departure from the expected array of functions was found in module 4. This module was expected to contain a DH domain, thereby directing the synthesis of epothilones C and D as the products of the PKS. Rigorous analysis revealed that the space between the AT and KR domains of module 4 was not large enough to accommodate a functional DH domain. Thus, the extent of reduction at module 4 does not proceed beyond the ketoreduction of the beta-keto formed after the condensation directed by module 4. Because the C-12,13 unsaturation has been demonstrated (epothilones C and D), there must be an additional dehydratase function that introduces the double bond. The dehydration reaction that mediates the formation of this double bond may be due to the action of an as yet unrecognized domain of the epothilone PKS (for example, dehydration could occur in the next module, which possesses an active DH domain and could generate a conjugated diene precursor prior to its dehydrogenation by an ER domain) or an endogenous enzyme in the host cells in which it is observed. As shown herein, the PKS genes and flanking sequences are sufficient to confer the ability to produce epothilones C and D in a host cell of the invention.

Thus, the action of the dehydratase could occur either during the synthesis of the polyketide or after cyclization has taken place. In the former case, the compounds produced at the end of acyl chain growth would be epothilones C and D.

If the C-12,13 dehydration were a post-polyketide event, the completed acyl chain would have a hydroxyl group at C-13, as shown below. The names epothilones G and H have been assigned to the 13-hydroxy compounds produced in the absence of or prior to the action of the dehydratase.

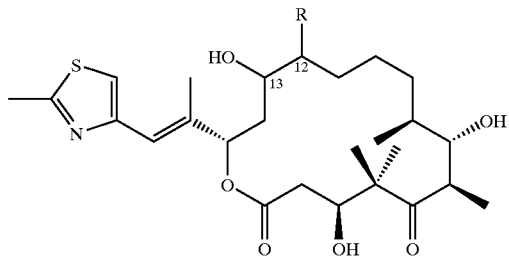

Epothilones G (R=H) and H (R=CH$_3$)

Modules 5 and 6 each have the full set of reduction domains (KR, DH and ER) to yield the methylene functions at C-11 and C-9. Modules 7 and 9 have KR domains to yield the hydroxyls at C-7 and C-3, and module 8 does not have a functional KR domain, consistent with the presence of the keto group at C-5. Module 8 also contains a methyltransferase (MT) domain that results in the presence of the geminal dimethyl function at C-4. Module 9 has a thioesterase domain that terminates polyketide synthesis and catalyzes ring closure.

The genes, proteins, modules, and domains of the epothilone PKS are summarized in the following Table.

| Gene | Protein | Modules | Domains Present |
|---|---|---|---|
| epoA | EpoA | Load | KS$^Y$ mAT ER ACP |
| epoB | EpoB | 1 | NRPS, condensation, heterocyclization, adenylation, thiolation, PCP |
| epoC | EpoC | 2 | KS mmAT DH KR ACP |
| epoD | EpoD | 3–6 | KS mAT KR ACP; KS mAT KR ACP; KS mAT DH ER KR ACP; KS mmAT DH ER KR ACP |
| epoE | EpoE | 7–8 | KS mmAT KR ACP; KS mmAT MT DH* KR* ACP |
| epoF | EpoF | 9 | KS mAT KR DH* ER* ACP TE |

NRPS—non-ribosomal peptide synthetase; KS—ketosynthase; mAT—malonyl CoA specifying acyltransferase; mmAT—methylmalonyl CoA specifying acyltransferase; DH—dehydratase; ER—enoylreductase; KR—ketoreductase; MT—methyltransferase; TE thioesterase; *—inactive domain.

Inspection of the sequence has revealed translational coupling between epoA and epoB (loading module and module 1) and between epoC and epoD. Very small gaps are seen between epoD and epoE and epoE and epoF but gaps exceeding 100 bp are found between epoB and epoC and epoF and epoK. These intergenic regions may contain promoters.

Thus, the epothilone PKS is multiprotein complex composed of the gene products of the epoA, epoB, epoC, epoD, epoE, and epoF genes. To confer the ability to produce epothilones to a host cell, one provides the host cell with the recombinant epoA, epoB, epoC, epoD, epoE, and epoF genes of the present invention, and optionally other genes, capable of expression in that host cell. Those of skill in the art will appreciate that, while the epothilone and other PKS enzymes may be referred to as a single entity herein, these enzymes are typically multisubunit proteins. Thus, one can make a derivative PKS (a PKS that differs from a naturally occurring PKS by deletion or mutation) or hybrid PKS (a PKS that is composed of portions of two different PKS enzymes) by altering one or more genes that encode one or more of the multiple proteins that constitute the PKS.

The post-PKS modification or tailoring of epothilone includes multiple steps mediated by multiple enzymes. These enzymes are referred to herein as tailoring or modification enzymes. Expression of the epothilone PKS genes epoA, epoB, epoC, epoD, epoE, and epoF in certain host cells of the invention that do not express epoK leads to the production of epothilones C and D, which lack the C-12-C-13 epoxide of epothilones A and B, having instead a C-12-C-13 double bond. Thus, epothilones C and D are converted to epothilones A and B by an epoxidase encoded by the epoK gene. Epothilones A and B are converted to epothilones E and F by a hydroxylase gene, which may be encoded by a gene associated with the epothilone PKS gene cluster or by another gene endogenous to *Sorangium cellulosum*. Thus, one can produce an epothilone or epothilone derivative modified as desired in a host cell by providing that host cell with one or more recombinant modification enzyme genes provided by the invention or by utilizing a host cell that naturally expresses (or does not express) the modification enzyme.

Thus, the present invention provides a wide variety of recombinant DNA compounds and host cells for expressing the naturally occurring epothilones A, B, C, and D and derivatives thereof. The invention also provides recombinant host cells that produce epothilone derivatives modified in a manner similar to epothilones E and F. Moreover, the invention provides host cells that can produce epothilones G and H, either by expression of the epothilone PKS genes in host cells that do not express the dehydratase that converts epothilones G and H to C and D or by mutating or altering the PKS to abolish the dehydratase function, if it is present in the epothilone PKS.

The present invention also provides a wide variety of recombinant DNA compounds and host cells that make epothilone derivatives. As used herein, the phrase epothilone derivative refers to a compound that is produced by a recombinant epothilone PKS in which at least one domain has been inserted or either rendered inactive, mutated to alter its catalytic function, or replaced by a domain with a different function. In any event, the epothilone derivative PKS so produced functions to produce a compound that differs in structure from a naturally occurring epothilone and so is called an epothilone derivative. To faciliate a better understanding of the recombinant DNA compounds and host cells provided by the invention, a detailed discussion of the loading module and each of the modules of the epothilone PKS, as well as novel recombinant derivatives thereof, is provided below.

The loading module of the epothilone PKS includes an "inactive" KS domain, designated KS$^Y$, that, due to the presence of a tyrosine (Y) residue in place of the cysteine residue found in "active" KS domains, is unable to perform the condensation reaction mediated by active KS doamains. The KS$^Y$ domain does carry out the decarboxylation reaction mediated by KS domains. Such "inactive" KS domains are found in other PKS enzymes, usually with a glutamine (Q) residue in place of the active site cysteine, and are called KS$^Q$ domains. The KS$^Q$ domain in rat fatty acid synthase has been shown to be unable to perform condensation but exhibits a 2 order of magnitude increase in decarboxylation. See Witkowski et al., Sep. 7, 1999, *Biochem.* 38(36): 11643–11650, incorporated herein by reference. A KS$^Q$ domain may be more efficient at decarboxylation than a $KS^Y$ domain, so the replacement of the $KS^Y$ domain in the epothilone PKS with a $KS^Q$ domain may increase the efficiency of epothilone biosynthesis. This can be accomplished merely by changing the codon from a tyrosine to a glutamine codon, as described in Example 6, below. This can also be accomplished by replacing the $KS^Y$ domain with a $KS^Q$ domain of another PKS, such as the oleandolide PKS or the narbonolide PKS (see the references cited in the Table above in connection with the oleandomycin, narbomycin, and picromycin PKS and modification enzymes).

The epothilone loading module also contains an AT domain specific for malonyl CoA (which is believed to be decarboxylated by the $KS^Y$ domain to yield an acetyl group), and an ACP domain. The present invention provides recombinant epothilone derivative loading modules or their encoding DNA sequences in which the malonyl specific AT domain or its encoding sequence has been changed to another specificity, such as methylmalonyl CoA, ethylmalonyl CoA, and 2-hydroxymalonyl CoA. When expressed with the other proteins of the epothilone PKS, such loading modules lead to the production of epothilones in which the methyl substituent of the thiazole ring of epothilone is replaced with, respectively, ethyl, propyl, and hydoxymethyl. The present invention provides recombinant PKS enzymes comprising such loading modules and host cells for producing such enzymes and the polyketides produced thereby. An AT domain specific for 2-hydroxymalonyl CoA will result in a polyketide with a hydroxyl group at the corresponding location in the polyketide produced; the hydroxyl group can be methylated to yield a methoxy group by polyketide modification enzymes. See, e.g., the references cited in connection with the FK-520 PKS in the Table above. Consequently, reference to a PKS that has a 2-hydroxymalonyl specific AT domain herein similarly refers to polyketides produced by that PKS that have either a hydroxyl or methoxyl group at the corresponding location in the polyketide.

The loading module of the epothilone PKS also comprises an ER domain. While, this ER domain may be involved in forming one of the double bonds in the thiazole moiety in epothilone (in the reverse of its normal reaction), it may be non-functional. In either event, the invention provides recombinant DNA compounds that encode the epothilone PKS loading module with and without the ER region, as well as hybrid loading modules that contain an ER domain from another PKS (either active or inactive, with or without accompanying KR and DH domains) in place of the ER domain of the epothilone loading module. The present invention also provides recombinant PKS enzymes comprising such loading modules and host cells for producing such enzymes and the polyketides produced thereby.

The loading module of the epothilone PKS is followed by the first extender module of the PKS, which is an NRPS module specific for cysteine. This NRPS module is naturally expressed as a discrete protein, the product of the epoB gene. In one embodiment, a portion of the NRPS module coding sequence is utilized in conjunction with a heterologous coding sequence. In this embodiment, the invention provides, for example, changing the specificity of the NRPS module of the epothilone PKS from a cysteine to another amino acid. This change is accomplished by constructing a coding sequence in which all or a portion of the epothilone PKS NRPS module coding sequences have been replaced by those coding for an NRPS module of a different specificity. In one illustrative embodiment, the specificity of the epothilone NRPS module is changed from cysteine to serine or threonine. When the thus modified NRPS module is expressed with the other proteins of the epothilone PKS, the recombinant PKS produces an epothilone derivative in which the thiazole moiety of epothilone (or an epothilone derivative) is changed to an oxazole or 5-methyloxazole moiety, respectively. Alternatively, the present invention provides recombinant PKS enzymes composed of the products of the epoA, epoC, epoD, epoE, and epoF genes (or modified versions thereof) without an NRPS module or with an NRPS module from a heterologous PKS. The heterologous NRPS module can be expressed as a discrete protein or as a fusion protein with either the epoA or epoC genes.

In another embodiment, the invention provides recombinant epothilone PKS enzymes and corresponding recombinant DNA compounds and vectors in which the NRPS module has been inactivated or deleted. Inactive NRPS module proteins and the coding sequences therefore provided by the invention include those in which the PCP domain has been wholly or partially deleted or otherwise rendered inactive by changing the active site serine (the site for phosphopantetheinylation) to another amino acid, such as alanine, or the adenylation domains have been deleted or otherwise rendered inactive. In one embodiment, both the loading module and the NRPS have been deleted or rendered inactive. In any event, the resulting epothilone PKS can then function only if provided a substrate that binds to the KS domain of module 2 (or a subsequent module) of the epothilone PKS or a PKS for an epothilone derivative. In a method provided by the invention, the thus modified cells are then fed activated acylthioesters that are bound by preferably the second, but potentially any subsequent, module and processed into novel epothilone derivatives. The host cell is fed activated acylthioesters to produce novel epothilone derivatives of the invention. The host cells expressing, or cell free extracts containing, the PKS can be fed or supplied with N-acylcysteanine thioesters (NACS) of novel precursor molecules to prepare epothilone derivatives. See U.S. patent application Ser. No. 09/492,733, filed Jan. 27, 2000, and PCT patent publication No. US99/03986, both of which are incorporated herein by reference, and Examples 9 and 10, below.

The second (first non-NRPS) extender module of the epothilone PKS includes a KS, an AT specific for methylmalonyl CoA, a DH, a KR, and an ACP. The second extender module of the epothilone PKS is produced as a discrete protein by the epoC gene. All or only a portion of the second extender module coding sequence can be utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with a DH or KR or both that specify a different stereochemistry; and/or inserting an ER. The resulting heterologous second extender module coding sequence can be coexpressed with the other proteins that constitute a PKS that synthesizes epothilone, an epothilone derivative, or another polyketide. Alternatively, one can delete or replace the second extender module of the epothilone PKS with a module from a heterologous PKS, which can be expressed as a discrete protein or as a fusion protein fused to either the epoB or epoD gene product.

Illustrative recombinant PKS genes of the invention include those in which the AT domain encoding sequences for the second extender module of the epothilone PKS have been altered or replaced to change the AT domain encoded thereby from a methylmalonyl specific AT to a malonyl specific AT. Such malonyl specific AT domain encoding nucleic acids can be isolated, for example and without limitation, from the PKS genes encoding the narbonolide PKS, the rapamycin PKS (i.e., modules 2 and 12), and the FK-520 PKS (i.e., modules 3, 7, and 8). When such a hybrid second extender module is coexpressed with the other proteins constituting the epothilone PKS, the resulting epothilone derivative produced is a 16-desmethyl epothilone. In a preferred embodiment, the hybrid PKS also contains a methylmalonyl CoA specific AT domain in extender module 4 and is epressed in a host cell lacking a functional epoK gene such that the compound produced is 16-desmethyl epothilone D In addition, the invention provides DNA compounds and vectors encoding recombinant epothilone PKS enzymes and the corresponding recombinant proteins in which the KS domain of the second (or subsequent) extender module has been inactivated or deleted, as described in Example 9, below. In a preferred embodiment, this inactivation is accomplished by changing the codon for the active site cysteine to an alanine codon. As with the corresponding variants described above for the NRPS module, the resulting recombinant epothilone PKS enzymes are unable to produce an epothilone or epothilone derivative unless supplied a precursor that can be bound and extended by the remaining domains and modules of the recombinant PKS enzyme. Illustrative precursor compounds are described in Example 10, below. Alternatively, one could simply provide such precursors to a host cell that expressed only the epoD, epoE, and epoF genes.

The third extender module of the epothilone PKS includes a KS, an AT specific for malonyl CoA, a KR, and an ACP. The third extender module of the epothilone PKS is expressed as a protein, the product of the epoD gene, which also contains modules 4, 5, and 6. To make a recombinant epothilone PKS that produces an epothilone derivative due to an alteration in any of extender modules 3 through 6, one typically expresses a protein comprising all four extender modules. In one embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR; replacing the KR with a KR that specifies a different stereochemistry; and/or inserting a DH or a DH and an ER. The resulting heterologous third extender module coding sequence can be utilized in conjunction with a coding sequence for a PKS that synthesizes epothilone, an epothilone derivative, or another polyketide.

Illustrative recombinant PKS genes of the invention include those in which the AT domain encoding sequences for the third extender module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When coexpressed with the remaining modules and proteins of the epothilone PKS or an epothilone PKS derivative, the recombinant PKS produces the 14-methyl epothilone derivatives of the invention.

Those of skill in the art will recognize that the KR domain of the third extender module of the PKS is responsible for forming the hydroxyl group involved in cyclization of epothilone. Consequently, abolishing the KR domain of the third extender module or adding a DH or DH and ER domains will interfere with the cyclization, leading either to a linear molecule or to a molecule cyclized at a different location than is epothilone.

The fourth extender module of the epothilone PKS includes a KS, an AT that can bind either malonyl CoA or methylmalonyl CoA, a KR, and an ACP. In one embodiment, all or a portion of the fourth extender module coding sequence is utilized in conjunction with other PKS coding sequences to create a hybrid module. In this embodiment, the invention provides, for example, either replacing the malonyl CoA and methylmalonyl specific AT with a malonyl CoA, methylmalonyl CoA, ethylmalonyl CoA, or 2-hydroxymalonyl CoA specific AT; deleting the KR; and/or replacing the KR, including, optionally, to specify a different stereochemistry; and/or inserting a DH or a DH and ER. The resulting heterologous fourth extender module coding sequence is incorporated into a protein subunit of a recombinant PKS that synthesizes epothilone, an epothilone derivative, or another polyketide. Alternatively, the invention provides recombinant PKS enzymes for epothilones and epothilone derivatives in which the entire fourth extender module has been deleted or replaced by a module from a heterologous PKS.

In a preferred embodiment, the invention provides recombinant DNA compounds comprising the coding sequence for the fourth extender module of the epothilone PKS modified to encode an AT that binds methylmalonyl CoA and not malonyl CoA. Thus, the invention provides recombinant DNA compounds and expression vectors and the corresponding recombinant PKS in which the hybrid fourth extender module with a methylmalonyl specific AT has been incorporated. The methylmalonyl specific AT coding sequence can originate, for example and without limitation, from coding sequences for the oleandolide PKS, DEBS, the narbonolide PKS, the rapamycin PKS, or any other PKS that comprises a methylmalonyl specific AT domain. In accordance with the invention, the hybrid fourth extender module expressed from this coding sequence is incorporated into the epothilone PKS (or the PKS for an epothilone derivative), typically as a derivative epoD gene product that comprises the modified fourth extender module as well as extender modules 3, 5, and 6, any one or more of which can optionally be in derivative form, of the epothilone PKS.

The recombinant methylmalonyl specific epothilone fourth extender module coding sequences provided by the invention afford important alternative methods for producing desired epothilone compounds in host cells. Thus, the invention provides a hybrid fourth extender module coding sequence in which, in addition to the replacement of the endogenous AT coding sequence with a coding sequence for an AT specific for methylmalonyl Co A, coding sequences for a DH and KR for, for example and without limitation, module 10 of the rapamycin PKS or modules 1 or 5 of the FK-520 PKS, have replaced the endogenous KR coding sequences. When the gene product comprising the hybrid fourth extender module and epothilone PKS modules 3, 5, and 6 (or derivatives thereof) encoded by this coding sequence is incorporated into a PKS comprising the other epothilone PKS proteins (or derivatives thereof) produced in a host cell, the cell makes either epothilone D or its trans stereoisomer (or derivatives thereof), depending on the stereochemical specificity of the inserted DH and KR domains.

Similarly, and as noted above, the invention provides recombinant DNA compounds comprising the coding sequence for the fourth extender module of the epothilone PKS modified to encode an AT that binds malonyl CoA and not methylmalonyl CoA. The invention provides recombinant DNA compounds and vectors and the corresponding recombinant PKS in which this hybrid fourth extender module has been incorporated into a derivative epoD gene product. When incorporated into the epothilone PKS (or the PKS for an epothilone derivative), the resulting recombinant epothilone PKS produces epothilones C, A, and E, depending, again, on whether epothilone modification enzymes are present. As noted above, depending on the host, whether the fourth extender module includes a KR and DH domain, and on whether and which of the dehydratase, epoxidase, and oxidase activities are present, the practitioner of the invention can produce one or more of the epothilone G, C, A, and E compounds and derivatives thereof using the compounds, host cells, and methods of the invention.

In another embodiment, the present invention provides the 13-oxo-epothilones by providing a recombinant epothilone PKS in which the KR domain of extender module 4 has been rendered inactive by mutation, delation, or replacement with a non-functional KR domain from another PKS. In a preferred embodiment, the invention provides a recombinant host cell that produces only 13-oxo-epothilone D, because the recombinant PKS also has a replacement of the AT domain of module 4 with a methylmalonyl specific AT domain, and no functional epoK gene is present in the cell. If the production of an epothilone derivative compound is low due to an alteration in a module, production may be improved by altering the KS and/or ACP domains of the succeeding module.

The fifth extender module of the epothilone PKS includes a KS, an AT that binds malonyl CoA, a DH, an ER, a KR, and an ACP. In one embodiment, a DNA compound comprising a sequence that encodes the fifth extender module of the epothilone PKS is inserted into a DNA compound that comprises coding sequences for the epothilone PKS or a recombinant epothilone PKS that produces an epothilone derivative. In another embodiment, a portion of the fifth extender module coding sequence is utilized in conjunction with other PKS coding sequences to create a hybrid module coding sequence and the hybrid module encoded thereby. In this embodiment, the invention provides, for example, either replacing the malonyl CoA specific AT with a methylmalonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. The resulting hybrid fifth extender module coding sequence can be utilized in conjunction with a coding sequence for a PKS that synthesizes epothilone, an epothilone derivative, or another polyketide. Alternatively, the fifth extender module of the epothilone PKS can be deleted or replaced in its entirety by a module of a heterologous PKS to produce a protein that in combination with the other proteins of the epothilone PKS or derivatives thereof constitutes a PKS that produces an epothilone derivative.

Illustrative recombinant PKS genes of the invention include recombinant epoD gene derivatives in which the AT domain encoding sequences for the fifth extender module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When such recombinant epoD gene derivatives are coexpressed with the epoA, epoB, epoC, epoE, and epoF genes (or derivatives thereof), the PKS composed thereof produces the 10-methyl epothilones or derivatives thereof. Another recombinant epoD gene derivative provided by the invention includes not only this altered module 5 coding sequence but also module 4 coding sequences that encode an AT domain that binds only methylmalonyl CoA. When incorporated into a PKS with the epoA, epoB, epoC, epoE, and epoF genes, the recombinant epoD gene derivative product leads to the production of 10-methyl epothilone B and/or D derivatives.

Other illustrative recombinant epoD gene derivatives of the invention include those in which the ER, DH, and KR domain encoding sequences for the fifth extender module of the epothilone PKS have been: (i) replaced with those encoding a KR and DH domain; (ii) either replaced with those encoding a KR domain or a KR domain and an inactive DH domain or from which the DH domain coding sequence has been deleted or rendered inactive by mutation; and (iii) either replaced with those encoding an inactive KR domain or from which the KR domain coding sequence has been deleted or rendered inactive by mutation. These recombinant epoD gene derivatives of the invention are coexpressed with the epoA, epoB, epoC, epoE, and epoF genes to produce a recombinant PKS that makes the corresponding (i) C-11 alkene, (ii) C-11 hydroxy (either epimer), and (iii) C-11 keto epothilone derivatives. These recombinant epoD gene derivatives can also be coexpressed with recombinant epo genes containing other alterations or can themselves be further altered to produce a PKS that makes the corresponding C-11 epothilone derivatives. For example, one recombinant epoD gene derivative provided by the invention also includes module 4 coding sequences that encode an AT domain that binds only methylmalonyl CoA. When incorporated into a PKS with the epoA, epoB, epoC, epoE, and epoF genes, the recombinant epoD gene derivative product leads to the production of the corresponding C-11 epothilone B and/or D derivatives, depending on whether a functional epoK gene is present in the host cell.

As noted above, functionally similar epoD genes for producing the epothilone C-11 derivatives can also be made by inactivation of one, two, or all three of the ER, DH, and KR domains of the epothilone fifth extender module. However, the preferred mode for altering such domains in any module is by replacement with the complete set of desired domains taken from another module of the same or a heterologous PKS coding sequence. In this manner, the natural architecture of the PKS is conserved. Also, when present, KR and DH or KR, DH, and ER domains that function together in a native PKS are preferably used in the recombinant PKS. Illustrative replacement domains for the substitutions described above include, for example and without limitation, the inactive KR domain from the rapamycin PKS module 3 to form the ketone, the KR domain from the rapamycin PKS module 5 to form the alcohol, and the KR and DH domains from the rapamycin PKS module 4 to form the alkene. Other such inactive KR, active KR, and active KR and DH domain encoding nucleic acids can be isolated from, for example and without limitation, the PKS genes encoding DEBS, the narbonolide PKS, and the FK-520 PKS. Each of the resulting PKS enzymes produces a polyketide compound that comprises a functional group at the C-11 position that can be further derivatized in vitro by standard chemical methodology to yield semi-synthetic epothilone derivatives of the invention.

The sixth extender module of the epothilone PKS includes a KS, an AT that binds methylmalonyl CoA, a DH, an ER, a KR, and an ACP. In one embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. The resulting heterologous sixth extender module coding sequence can be utilized in conjunction with a coding sequence for a protein subunit of a PKS that makes epothilone, an epothilone derivative, or another polyketide. Alternatively, the sixth extender module of the epothilone PKS can be deleted or replaced in its entirety by a module from a heterologous PKS to produce a PKS for an epothilone derivative.

Illustrative recombinant PKS genes of the invention include those in which the AT domain encoding sequences for the sixth extender module of the epothilone PKS have been altered or replaced to change the AT domain encoded thereby from a methylmalonyl specific AT to a malonyl specific AT. Such malonyl specific AT domain encoding nucleic acids can be isolated from, for example and without limitation, the PKS genes encoding the narbonolide PKS, the rapamycin PKS, and the FK-520 PKS. When a recombinant epoD gene of the invention encoding such a hybrid module 6 is coexpressed with the other epothilone PKS genes, the recombinant PKS makes the 8-desmethyl epothilone derivatives. This recombinant epoD gene derivative can also be coexpressed with recombinant epo gene derivatives containing other alterations or can itself be further altered to produce a PKS that makes the corresponding 8-desmethyl epothilone derivatives. For example, one recombinant epoD gene provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the 8-desmethyl derivatives of epothilones B and D.

Other illustrative recombinant epoD gene derivatives of the invention include those in which the ER, DH, and KR domain encoding sequences for the sixth extender module of the epothilone PKS have been replaced with those that encode (i) a KR and DH domain; (ii) a KR domain; and (iii) an inactive KR domain. These recombinant epoD gene derivatives of the invention, when coexpressed with the other epothilone PKS genes make the corresponding (i) C-9 alkene, (ii) C-9 hydroxy (both epimers, only one of which may be processed by downstream modules, unless additional KS and/or ACP replacements are made in the next module), and (iii) C-9 keto (C-9-oxo) epothilone derivatives. Functionally equivalent sixth extender modules can also be made by inactivation of one, two, or all three of the ER, DH, and KR domains of the epothilone sixth extender module. These recombinant epoD gene derivatives can also be coexpressed with other recombinant epo gene derivatives containing other alterations or can themselves be further altered to produce a PKS that makes the corresponding C-9 epothilone derivatives. For example, one recombinant epoD gene derivative provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the C-9 derivatives of epothilones B and D, depending on whether a functional epoK gene is present.

Illustrative replacement domains for the substitutions described above include but are not limited to the inactive KR domain from the rapamycin PKS module 3 to form the ketone, the KR domain from the rapamycin PKS module 5 to form the alcohol, and the KR and DH domains from the rapamycin PKS module 4 to form the alkene. Other such inactive KR, active KR, and active KR and DH domain encoding nucleic acids can be isolated from for example and without limitation the PKS genes encoding DEBS, the narbonolide PKS, and the FK-520 PKS. Each of the resulting PKSs produces a polyketide compound that comprises a functional group at the C-9 position that can be further derivatized in vitro by standard chemical methodology to yield semi-synthetic epothilone derivatives of the invention.

The seventh extender module of the epothilone PKS includes a KS, an AT specific for methylmalonyl CoA, a KR, and an ACP. The seventh extender module of the epothilone PKS is contained in the gene product of the epoE gene, which also contains the eighth extender module. In one embodiment, a DNA compound comprising a sequence that encodes the seventh extender module of the epothilone PKS is expressed to form a protein that, together with other proteins, constitutes the epothilone PKS or a PKS that produces an epothilone derivative. In these and related embodiments, the seventh and eighth extender modules of the epothilone PKS or a derivative thereof are typically expressed as a single protein and coexpressed with the epoA, epoB, epoC, epoD, and epoF genes or derivatives thereof to constitute the PKS. In another embodiment, a portion or all of the seventh extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR; replacing the KR with a KR that specifies a different stereochemistry; and/or inserting a DH or a DH and an ER. The resulting heterologous seventh extender module coding sequence is utilized, optionally in conjunction with other coding sequences, to express a protein that together with other proteins constitutes a PKS that synthesizes epothilone, an epothilone derivative, or another polyketide. Alternatively, the coding sequences for the seventh extender module in the epoE gene can be deleted or replaced by those for a heterologous module to prepare a recombinant epoE gene derivative that, together with the epoA, epoB, epoC, epoD, and epoF genes, can be expressed to make a PKS for an epothilone derivative.

Illustrative recombinant epoE gene derivatives of the invention include those in which the AT domain encoding sequences for the seventh extender module of the epothilone PKS have been altered or replaced to change the AT domain encoded thereby from a methylmalonyl specific AT to a malonyl specific AT. Such malonyl specific AT domain encoding nucleic acids can be isolated from for example and without limitation the PKS genes encoding the narbonolide PKS, the rapamycin PKS, and the FK-520 PKS. When coexpressed with the other epothilone PKS genes, epoA, epoB, epoC, epoD, and epoF, or derivatives thereof, a PKS for an epothilone derivative with a C-6 hydrogen, instead of a C-6 methyl, is produced. Thus, if the genes contain no other alterations, the compounds produced are the 6-desmethyl epothilones.

The eighth extender module of the epothilone PKS includes a KS, an AT specific for methylmalonyl CoA, inactive KR and DH domains, a methyltransferase (MT) domain, and an ACP. In one embodiment, a DNA compound comprising a sequence that encodes the eighth extender module of the epothilone PKS is coexpressed with the other proteins constituting the epothilone PKS or a PKS that produces an epothilone derivative. In another embodiment, a portion or all of the eighth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the inactive KR and/or the inactive DH; replacing the inactive KR and/or DH with an active KR and/or DH; and/or inserting an ER. The resulting heterologous eighth extender module coding sequence is expressed as a protein that is utilized in conjunction with the other proteins that constitute a PKS that synthesizes epothilone, an epothilone derivative, or another polyketide. Alternatively, the coding sequences for the eighth extender module in the epoE gene can be deleted or replaced by those for a heterologous module to prepare a recombinant epoE gene that, together with the epoA, epoB, epoC, epoD, and epoF genes, can be expressed to make a PKS for an epothilone derivative.

The eighth extender module of the epothilone PKS also comprises a methylation or methyltransferase (MT) domain with an activity that methylates the epothilone precursor. This function can be deleted to produce a recombinant epoD gene derivative of the invention, which can be expressed with the other epothilone PKS genes or derivatives thereof that makes an epothilone derivative that lacks one or both methyl groups, depending on whether the AT domain of the eighth extender module has been changed to a malonyl specific AT domain, at the corresponding C-4 position of the epothilone molecule.

The ninth extender module of the epothilone PKS includes a KS, an AT specific for malonyl CoA, a KR, an inactive DH, and an ACP. The ninth extender module of the epothilone PKS is expressed as a protein, the product of the epoF gene, that also contains the TE domain of the epothilone PKS. In one embodiment, a DNA compound comprising a sequence that encodes the ninth extender module of the epothilone PKS is expressed as a protein together with other proteins to constitute an epothilone PKS or a PKS that produces an epothilone derivative. In these embodiments, the ninth extender module is typically expressed as a protein that also contains the TE domain of either the epothilone PKS or a heterologous PKS. In another embodiment, a portion or all of the ninth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxy malonyl CoA specific AT; deleting the KR; replacing the KR with a KR that specifies a different stereochemistry; and/or inserting a DH or a DH and an ER. The resulting heterologous ninth extender module coding sequence is coexpressed with the other proteins constituting a PKS that synthesizes epothilone, an epothilone derivative, or another polyketide. Alternatively, the present invention provides a PKS for an epothilone or epothilone derivative in which the ninth extender module has been replaced by a module from a heterologous PKS or has been deleted in its entirety. In the latter embodiment, the TE domain is expressed as a discrete protein or fused to the eighth extender module.

Illustrative examples of recombinant epothilone derivative PKS genes of the invention, which are identified by listing the altered specificities of the hybrid modules (the other modules having the same specificity as the epothilone PKS), include:

(a) module 4 with methylmalonyl specific AT (mmAT) and a KR and module 2 with a malonyl specific AT (mAT) and a KR;
(b) module 4 with mmAT and module 3 with mmAT;
(c) module 4 with mmAT and module 5 with mmAT;
(d) module 4 with mmAT and module 5 with mmAT and only a DH and KR;
(e) module 4 with mmAT and module 5 with mmAT and only a KR;
(f) module 4 with mmAT and module 5 with mmAT and only an inactive KR;
(g) module 4 with mmAT and module 6 with mAT;
(h) module 4 with mmAT and module 6 with mAT and only a DH and KR;
(i) module 4 with mmAT and module 6 with mAT and only a KR;
(j) module 4 with mAT and module 6 with mAT and only an inactive KR;
(k) module 4 with mmAT and module 7 with mAT;
(l) hybrids (d) through (f), except that module 5 has an mAT;
(m) hybrids (h) through (j) except that module 6 has an mmAT; and
(n) hybrids (a) through (m) except that module 4 has an mAT.

The above list is illustrative only and should not be construed as limiting the invention, which includes other recombinant epothilone PKS genes and enzymes with not only two hybrid modules other than those shown but also with three or more hybrid modules.

The host cells of the invention can be grown and fermented under conditions known in the art for other purposes to produce the compounds of the invention. The compounds of the invention can be isolated from the fermentation broths of these cultured cells and purified by methods such as those in Example 3, below.

Thus, in another embodiment, the present invention provides novel epothilone derivative compounds in isolated and substantially pure forms useful in agriculture, veterinary practice, and medicine. The term isolated refers to a compound or composition in a preparation that is substantially free of contaminating or undesired materials or, with respect to a compound or composition found in nature, substantially free of the materials with which that compound or composition is associated in its natural state. In one embodiment, the compounds are useful as fungicides. In another embodiment, the compounds are useful in cancer chemotherapy. In a preferred embodiment, the compound is an epothilone derivative that is at least as potent against tumor cells as epothilone B or D. In another embodiment, the compounds are useful as immunosuppressants. In another embodiment, the compounds are useful in the manufacture of another compound. In a preferred embodiment, the compounds are formulated in a mixture or solution for administration to a human or animal.

The novel epothilone analogs of the present invention, as well as the epothilones produced by the host cells of the invention, can be derivatized and formulated as described in PCT patent publication Nos. 93/10121, 97/19086, 98/08849, 98/22461, 98/25929, 99/01124, 99/02514, 99/07692, 99/27890, 99/39694, 99/40047, 99/42602, 99/43320, 99/43653, 99/54318, 99/54319, 99/54330, 99/65913, 99/67252, 99/67253, and 00/00485, and U.S. Pat. No. 5,969, 145, each of which is incorporated herein by reference.

Preferred compounds of the invention include the 14-methyl epothilone derivatives (made by utilization of the hybrid module 3 of the invention that has an AT that binds methylmalonyl CoA instead of malonyl CoA); the 8,9-dehydro epothilone derivatives (made by utilization of the hybrid module 6 of the invention that has a DH and KR instead of an ER, DH, and KR); the 10-methyl epothilone derivatives (made by utilization of the hybrid module 5 of the invention that has an AT that binds methylmalonyl CoA instead of malonyl CoA); the 9-hydroxy epothilone derivatives (made by utilization of the hybrid module 6 of the invention that has a KR instead of an ER, DH, and KR); the 8-desmethyl-14-methyl epothilone derivatives (made by utilization of the hybrid module 3 of the invention that has an AT that binds methylmalonyl CoA instead of malonyl CoA and a hybrid module 6 that binds malonyl CoA instead of methylmalonyl CoA); and the 8-desmethyl-8,9-dehydro epothilone derivatives (made by utilization of the hybrid module 6 of the invention that has a DH and KR instead of an ER, DH, and KR and an AT that specifies malonyl CoA instead of methylmalonyl CoA). Illustrative examples of other preferred novel epothilones of the invention that can be made using epothilone derivative PKS enzymes of the invention include 9-oxo-11-hydroxy-epothilone D (module 4 AT replacement, module 6 KR inactivation, and module 5 DH inactivation); 9-hydroxy-11-oxo-epothilone D (module 4 AT replacement, module 6 DH inactivation, and module 5 KR inactivation); and 9,11-dihydroxy-epothilone D (module 4 AT replacement, module 6 DH inactivation, and module 5 DH inactivation).

The compounds of the invention can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17–22, incorporated herein by reference. Dosage forms for external application may be prepared essentially as described in EP Pub. No. 423,714, incorporated herein by reference. The active compound is included in the pharmaceutical composition in an amount sufficient to produce the desired effect upon the disease process or condition.

For the treatment of conditions and diseases caused by infection, immune system disorder (or to suppress inmmune function), or cancer, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intrathecal, intramuscular, and intrasternal injection or infusion techniques.

Dosage levels of the compounds of the present invention are of the order from about 0.01 mg to about 100 mg per kilogram of body weight per day, preferably from about 0.1 mg to about 50 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particlular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

In another embodiment, the present invention provides a method of treating cancer, which method comprises administering a therapeutically effective amount of a novel epothilone compound of the invention.

A detailed description of the invention having been provided above, the following examples are given for the purpose of illustrating the present invention and shall not be construed as being a limitation on the scope of the invention or claims.

EXAMPLE 1

Construction of a *Myxococcus xanthus* Expression Vector

The DNA providing the integration and attachment function of phage Mx8 was inserted into commercially available pACYC184 (New England Biolabs). An ~2360 bp MfeI-SmaI from plasmid pPLH343, described in Salmi et al., Feb. 1998, *J. Bact.* 180(3): 614–621, was isolated and ligated to the large EcoRI-XmnI restriction fragment of plasmid pACYC184. The circular DNA thus formed was ~6 kb in size and called plasmid pKOS35-77.

Plasmid pKOS35-77 serves as a convenient plasmid for expressing recombinant PKS genes of the invention under the control of the epothilone PKS gene promoter. In one illustrative embodiment, the entire epothilone PKS gene with its homologous promoter is inserted in one or more fragments into the plasmid to yield an expression vector of the invention.

The present invention also provides expression vectors in which the recombinant PKS genes of the invention are under the control of a *Myxococcus xanthus* promoter. To construct an illustrative vector, the promoter of the pila gene of *M. xanthus* was isolated as a PCR amplification product. Plasmid pSWU357, which comprises the pilA gene promoter and is described in Wu and Kaiser, Dec. 1997, *J Bact.* 179(24):7748–7758, was mixed with PCR primers Seq1 and Mxpi11 primers:

Seq 1:
5'-AGCGGATAACAATTTCACACAGGAAACAGC-3' (SEQ ID NO:1); and

Mxpi11:
5'-TTAATTAAGAGAAGGTTGCAACGGGGGGC-3' (SEQ ID NO:2), and amplified using standard PCR conditions to yield an ~800 bp fragment. This fragment was cleaved with restriction enzyme KpnI and ligated to the large KpnI-EcoRV restriction fragment of commercially available plasmid pLitmus 28 (New England Biolabs). The resulting circular DNA was designated plasmid pKOS35-71B.

The promoter of the pilA gene from plasmid pKOS35-71B was isolated as an ~800 bp EcoRV-SnaBI restriction fragment and ligated with the large MscI restriction fragment of plasmid pKOS35-77 to yield a circular DNA ~6.8 kb in size. Because the ~800 bp fragment could be inserted in either one of two orientations, the ligation produced two plasmids of the same size, which were designated as plasmids pKOS35-82.1 and pKOS35-82.2. Restriction site and function maps of these plasmids are presented in FIG. 2.

Plasmids pKOS35-82.1 and pKOS35-82.2 serve as convenient starting materials for the vectors of the invention in which a recombinant PKS gene is placed under the control of the *Myxococcus xanthus* pilA gene promoter. These plasmids comprise a single PacI restriction enzyme recognition sequence placed immediately downstream of the transcription start site of the promoter. In one illustrative embodiment, the entire epothilone PKS gene without its homologous promoter is inserted in one or more fragments into the plasmids at the PacI site to yield expression vectors of the invention.

The sequence of the pilA promoter in these plasmids is shown below (SEQ ID NO:3).
CGACGCAGGTGAAGCTGCTTCGTGT-
GCTCCAGGAGCGGAAGGTGAAGCCGGTC
GGCAGCGCCGCGGAGATTCCCTTCCAG-
GCGCGTGTCATCGCGGCAACGAACCG GCGGCTC-
GAAGCCGAAGTAAAGGCCG-
GACGCTTTCGTGAGGACCTCTTCTACCG
GCTCAACGTCATCACGTTGGAGCTGC-
CTCCACTGCGCGAGCGTTCCGGCGACGT GTCGT-
TGCTGGCGAACTACTTCCTGTCCAGACT-
GTCGGAGGAGTTGGGGCGACC
CGGTCTGCGTTTCTCCCCCGAGA-
CACTGGGGCTATTGGAGCGCTATCCCTTCCCA
GGCAACGTGCGGCAGCTGCAGAACATG-
GTGGAGCGGGCCGCGACCCTGTCGGA TTCAGAC-
CTCCTGGGGCCCTCCACGCTTCCACCCG-
CAGTGCGGGCGATACAGA
CCCCGCCGTGCGTCCCGTGGAGGGCAGT-
GAGCCAGGGCTGGTGGCGGGCTTCA ACCTG-
GAGCGGCATCTCGACGACAGCGAGCG-
GCGCTATCTCGTCGCGGCGATG
AAGCAGGCCGGGGGCGTGAAGACCCGT-
GCTGCGGAGTTGCTGGGCCTTTCGTTC CGTTCAT-
TCCGCTACCGGTTGGCCAAGCATGGGCT-
GACGGATGACTTGGAGCCC
GGGAGCGCTTCGGATGCGTAGGCTGATC-
GACAGTTATCGTCAGCGTCACTGCCG AATTTTGT-
CAGCCCTGGACCCATCCTCGCCGAGGG-
GATTGTTCCAAGCCTTGAG
AATTGGGGGGCTTGGAGTGCGCAC-
CTGGGTTGGCATGCGTAGTGCTAATCCCAT
CCGCGGGCGCAGTGCCCCCCGTTGCAAC-
CTTCTCTTAATTAA To make the recombinant *Myxococcus xanthus* host cells of the invention, *M. xanthus* cells are grown in CYE media (Campos and Zusman, 1975, Regulation of development in *Myxococcus xanthus*: effect of 3':5'-cyclic AMP, ADP, and nutrition, *Proc. Natl. Acad. Sci. USA* 72: 518–522) to a Klett of 100 at 30° C. at 300 rpm. The remainder of the protocol is conducted at 25° C. unless otherwise indicated. The cells are then pelleted by centrifugation (8000 rpm for 10 min. in an SS34 or SA600 rotor) and resuspended in deionized water. The cells are again pelleted and resuspended in 1/100th of the original volume.

DNA (one to two µL) is electroporated into the cells in a 0.1 cm cuvette at room temperature at 400 ohm, 25 µFD, 0.65 V with a time constant in the range of 8.8–9.4. The DNA is free of salts and is resuspended in distilled and deionized water or dialyzed on a 0.025 µm Type VS membrane (Millipore). For low efficiency electroporations, the DNA is spot dialyzed, and outgrowth is in CYE. Immediately after electroporation, 1 mL of CYE is added, and the cells in the cuvette pooled with an additional 1.5 mL of CYE previously added to a 50 mL Erlenmeyer flask (total volume 2.5 ml). The cells are grown for four to eight hours (or overnight) at 30 to 32° C. at 300 rpm to allow for expression of the selectable marker. Then, the cells are plated in CYE soft agar on plates with selection. With kanamycin as the selectable marker, typical yields are $10^3$ to $10^5$ per µg of DNA. With streptomycin as the selectable marker, it is included in the top agar, because it binds agar.

With this procedure, the recombinant DNA expression vectors of the invention are electroporated into Myxococcus host cells that express recombinant PKSs of the invention and produce the epothilone, epothilone derivatives, and other novel polyketides encoded thereby.

EXAMPLE 2

Construction of a Bacterial Artificial Chromosome (BAC) for Expression of Epothilone in *Myxococcus xanthus*

To express the epothilone PKS and modification enzyme genes in a heterologous host to produce epothilones by fermentation, *Myxococcus xanthus*, which is closely related to *Sorangium cellulosum* and for which a number of cloning vectors are available, is employed in accordance with the methods of the invention. *M. xanthus* and *S. cellulosum* are myxobacteria and so may share common elements of gene expression, translational control, and post translational modification (if any). *M. xanthus* has been developed for gene cloning and expression: DNA can be introduced by electroporation, and a number of vectors and genetic markers are available for the introduction of foreign DNA, including those that permit its stable insertion into the chromosome. *M. xanthus* can be grown with relative ease in complex media in fermentors and can be subjected to manipulations to increase gene expression, if required.

To introduce the epothilone gene cluster into *Myxococcus xanthus*, one can build the epothilone cluster into the chromosome by using homologous recombination to assemble the complete gene cluster. Alternatively, the complete epothilone gene cluster can be cloned on a bacterial artificial chromosome (BAC) and then moved into *M. xanthus* for integration into the chromosome.

Figure 3:
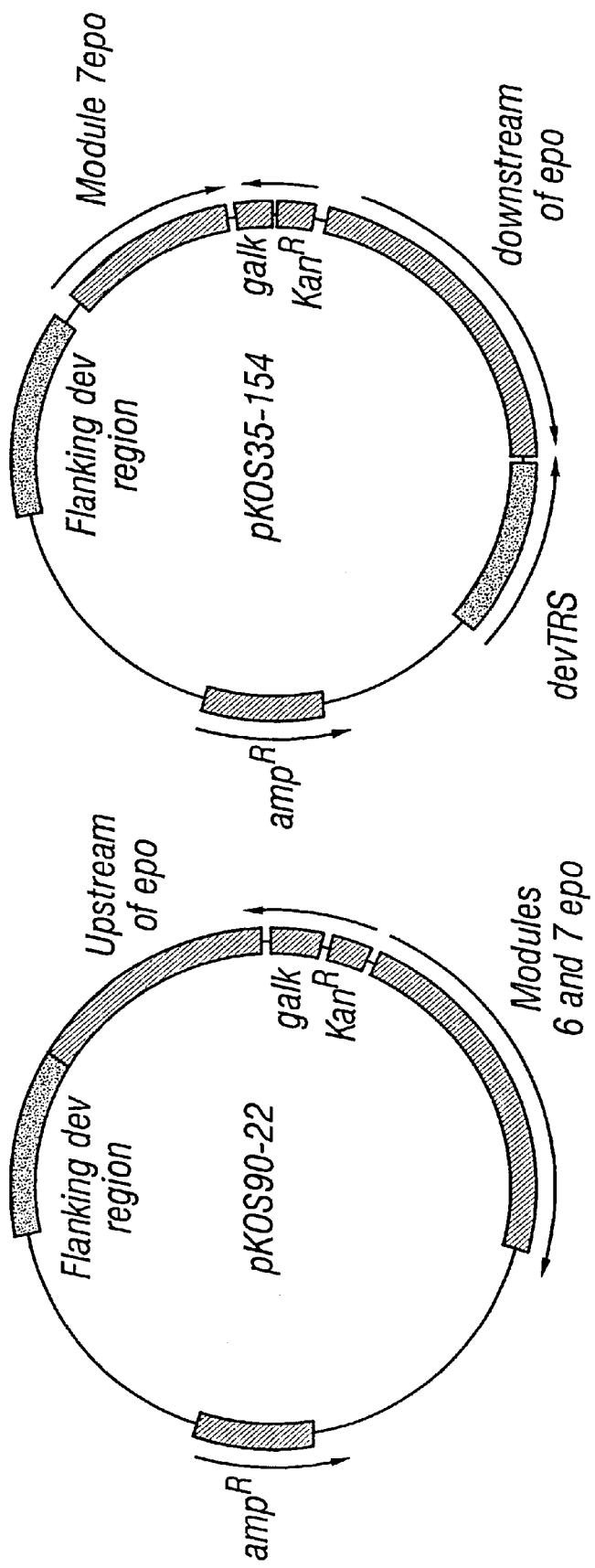
FIG. 3 shows restriction site and function maps of plasmids pKOS35-154 and pKOS90-22.
Figure 4:
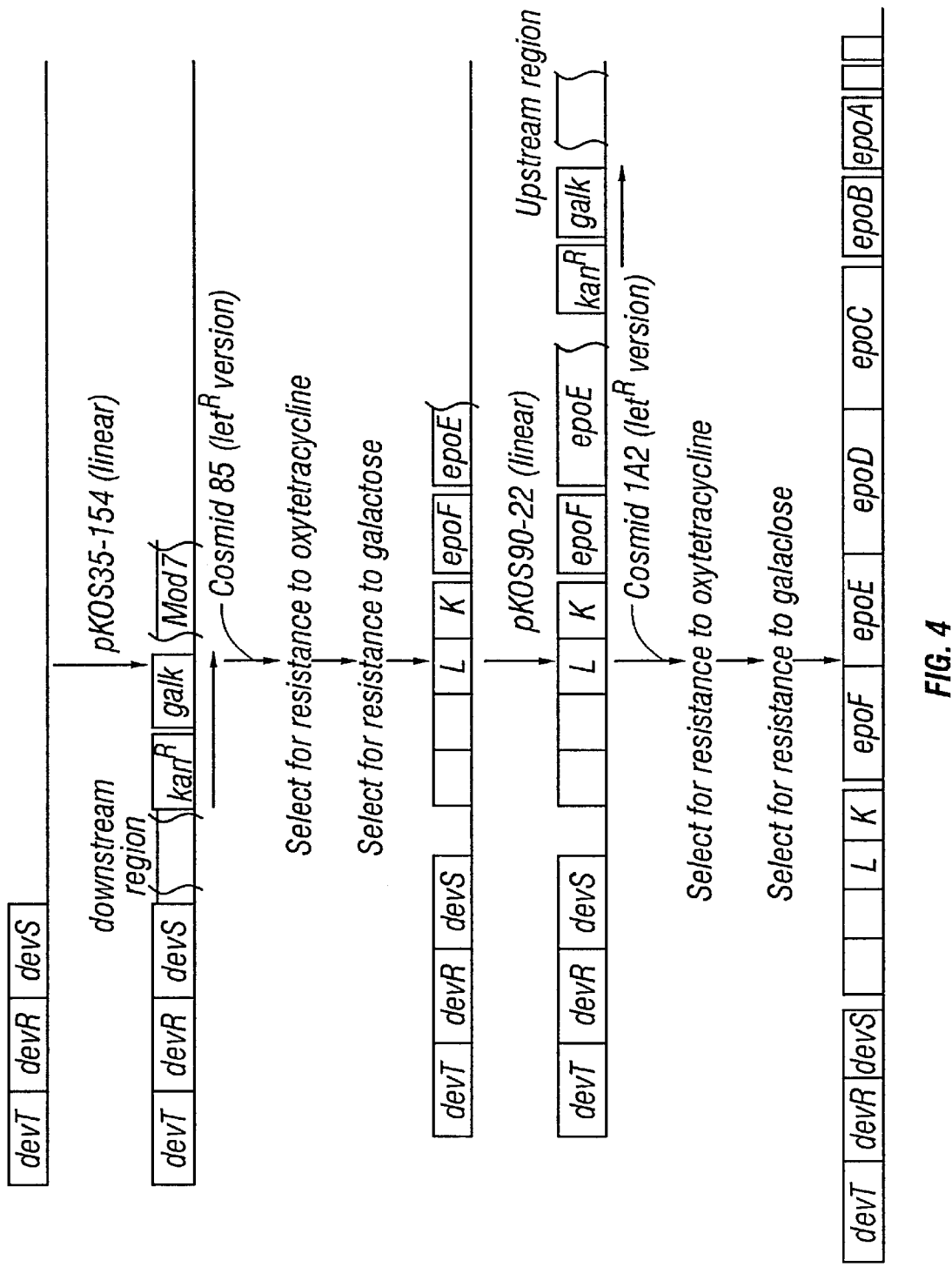
FIG. 4 shows a schematic of a protocol for introducing the epothilone PKS and modification enzyme genes into the chromosome of a *Myxococcus xanthus* host cell as described in Example 3.

To assemble the gene cluster from cosmids pKOS35-70.1A2, and pKOS35-79.85, small regions (~2 kb or larger) of homology from these cosmids are introduced into *Myxococcus xanthus* to provide recombination sites for larger pieces of the gene cluster. As shown in FIG. 3, plasmids pKOS35-154 and pKOS90-22 are created to introduce these recombination sites. The strategy for assembling the epothilone gene cluster in the *M. xanthus* chromosome is shown in FIG. 4. Initially, a neutral site in the bacterial chromosome is chosen that does not disrupt any genes or transcriptional units. One such region is downstream of the devS gene, which has been shown not to affect the growth or development of *M. xanthus*. The first plasmid, pKOS35-154, is linearized with DraI and electroporated into *M. xanthus*. This plasmid contains two regions of the dev locus flanking two fragments of the epothilone gene cluster. Inserted in between the epo gene regions is a cassette composed of a kanamycin resistance marker and the *E. coli* galK gene. See Ueki et al., 1996, *Gene* 183: 153–157, incorporated herein by reference. Kanamycin resistance arises in colonies if the DNA recombines into the dev region by a double recombination using the dev sequence as regions of homology.

This strain, K35-159, contains small (~2.5 kb) regions of the epothilone gene cluster that will allow for recombination of pKOS35-79.85. Because the resistance markers on pKOS35-79.85 are the same as that in K35-159, a tetracycline transposon was transposed into the cosmid, and cosmids that contain the transposon inserted into the kanamycin marker were selected. This cosmid, pKOS90-23, was electroporated into K35-159, and oxytetracycline resistant colonies were selected to create strain K35-174. To remove the unwanted regions from the cosmid and leave only the epothilone genes, cells were plated on CYE plates containing 1% galactose. The presence of the galK gene makes the cells sensitive to 1% galactose. Galactose resistant colonies of K35-174 represent cells that have lost the galK marker by recombination or by a mutation in the galK gene. If the recombination event occurs, then the galactose resistant strain is sensitive to kanamycin and oxytetracycline. Strains sensitive to both antibiotics are verified by Southern blot analysis. The correct strain is identified and designated K35-175 and contains the epothilone gene cluster from module 7 to 4680 bp downstream of the stop codon of epoK.

To introduce modules 1 through module 7, the above process is repeated once more. The plasmid pKOS90-22 is linearized with DraI and electroporated into K35-175 to create K111-13.2. This strain is electroporated with the tetracycline resistant version of pKOS35-70.1A2, pKOS90-38, and colonies resistant to oxytetracycline are selected. This creates strain K111-13.23. Recombinants that now have the whole epothilone gene cluster are selected by resistance to 1% galactose. This results in clones K111-32.25, K111-32.26, and K111-32.35. Strain K111-32.25 has been deposited with the American Type Culture Collection, 10801 University Blvd., Manassas, Va. 20110-2209, on April 14, 2000 in compliance with the Budapest Treaty and is available under accession No. PTA-1700. All restrictions on access to this deposit will be irrevocably removed upon issuance of a U.S. patent on this application. This strain contains all the epothilone genes and their promoters.

Fermentation was performed by inoculating strains into 5 mL of CYE in a 50 mL flask and growing overnight until the culture was in mid log growth phase. A 100 $\mu$L aliquot was spread onto a CTS plate, and the plate incubated at 32° C. for 4 to 5 days. To extract epothilones, the agar plate with cells was macerated, put in a 50 mL conical tube, and acetone added to fill the tube. The solution was incubated with rocking for 4 to 5 hours, the acetone evaporated, and the remaining liquid extracted twice with an equal volume of ethyl acetate. The water was removed from the ethyl acetate extract by adding magnesium sulfate. The magnesium sulfate was filtered out, and the liquid was evaporated to dryness. The epothilones were resuspended in 200 $\mu$L of acetonitrile and analyzed by LC/MS. The analysis showed that the strain produced epothilones A and B, with epothilone B present at about 0.5 mg/L in the culture, and epothilone A at 5 to 10-fold lower levels.

Alternatively, this strain can be used to produce epothilones in liquid culture. A flask containing CYE is inoculated with an epothilone producing strain. The next day, while the cells are in mid-log growth phase, a 5% inoculum is added to a flask containing 0.5% CMM (0.5% casitone, 0.2% MgSO4.7H2O, 10 mM MOPS pH7.6) along with 1 mg/ml serine, alanine, and glycine and 0.1% sodium puyruvate. The sodium pyruvate can be added to 0.5% to increase epothilone B production but causes a decrease in the ratio of epothilone B to epothilone A. The culture is grown at 30° C. for 60–72 hours. Longer incubations result in a decrease in titers of epothilones. To recover epothilones, the cultures are centrifuged at 10,000 rpm for 10 minutes in an SS34 rotor. The supernatants are extracted twice with ethyl acetate and rotavaped to dryness. Liquid cultures produced 2 to 3 mg/L of epothilones A and B, with ratios similar to that observed with plate cultures. If XAD (0.5–2%) was added to the culture, epothilones C and D were observed, with epothilone D present at 0.5 to 1 mg/L and epothilone C present at 5 to 10-fold lower levels.

To clone the whole gene cluster as one fragment, a bacterial artifical chromosome (BAC) library is constructed. First, SMP44 cells are embedded in agarose and lysed according to the BIO-RAD genomic DNA plug kit. DNA plugs are partially digested with restriction enzyme, such as Sau3AI or HindIII, and electrophoresed on a FIGE or CHEF gel. DNA fragments are isolated by electroeluting the DNA from the agarose or using gelase to degrade the agarose. The method of choice to isolate the fragments is electroelution, as described in Strong et al., 1997, *Nucleic Acids Res.* 19: 3959–3961, incorporated herein by reference. The DNA is ligated into the BAC (pBeloBACII) cleaved with the appropriate enzyme. A map of pBeloBACII is shown below.

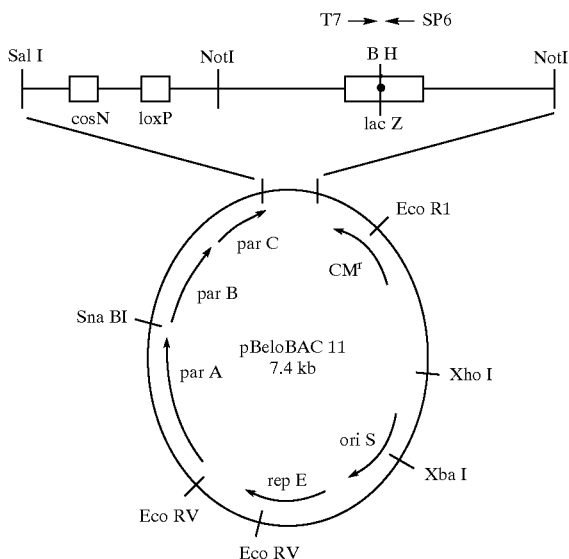

The DNA is electroporated into DH10B cells by the method of Sheng et al., 1995, *Nucleic Acids Res.* 23: 1990–1996, incorporated herein by reference, to create a *Sorangium cellulosum* genomic library. Colonies are screened using a probe from the NRPS region of the epothilone cluster. Positive clones are picked and DNA is isolated for restriction analysis to confirm the presence of the complete gene cluster. This positive clone is designated pKOS35-178.

To create a strain that can be used to introduce pKOS35-178, a plasmid, pKOS35-164, is constructed that contains regions of homology that are upstream and downstream of the epothilone gene cluster flanked by the dev locus and containing the kanamycin resistance galK cassette, analogous to plasmids pKOS90-22 and pKOS35-154. This plasmid is linearized with DraI and electroporated into *Myxococcus xanthus*, in accordance with the method of Kafeshi et al., 1995, *Mol. Microbiol.* 15: 483–494, to create K35-183. The plasmid pKOS35-178 can be introduced into K35–183 by electroporation or by transduction with bacteriophage P1, and chloramphenicol resistant colonies are selected. Alternatively, a version of pKOS35-178 that contains the origin of conjugative transfer from pRP4 can be constructed for transfer of DNA from *E. coli* to K35-183. This plasmid is made by first constructing a transposon containing the oriT region from RP4 and the tetracycline resistance maker from pACYC184 and then transposing the transposon in vitro or in vivo onto pKOS35-178. This plasmid is transformed into S17-1 and conjugated into *M. xanthus*. This strain, K35-190, is grown in the presence of 1% galactose to select for the second recombination event. This strain contains all the epothilone genes as well as all potential promoters. This strain is fermented and tested for the production of epothilones A and B.

Alternatively, the transposon can be recombined into the BAC using either the temperature sensitive plasmid pMAK705 or pKO3 by transposing the transposon onto either pMAK705 or pKO3, selecting for tetR and camS plasmids; the recombination is accomplished as described in Hamilton et al., Sep. 1989, *J. Bact.* 171(9): 4617–4622 and Link et al., Oct. 1997, *J. Bact.* 179(20): 6228–6237, each of which is incorporated herein by reference.

Besides integrating pKOS35-178 into the dev locus, it can also be integrated into a phage attachment site using integration functions from myxophages Mx8 or Mx9. A transposon is constructed that contains the integration genes and att site from either Mx8 or Mx9 along with the tetracycline gene from pACYC184. Alternative versions of this transposon may have only the attachment site. In this version, the integration genes are then supplied in trans by coelectroporation of a plasmid containing the integrase gene or having the integrase protein expressed in the electroporated strain from any constitutive promoter, such as the mgl promoter (see Magrini et al., Jul. 1999, *J. Bact.* 181(13): 4062–4070, incorporated herein by reference). Once the transposon is constructed, it is transposed onto pKOS35-178 to create pKOS35-191. This plasmid is introduced into *Myxococcus xanthus* as described above. This strain contains all the epothilone genes as well as all potential promoters. This strain is fermented and tested for the production of epothilones A and B.

Once the epothilone genes have been established in a strain of *Myxococcus xanthus*, manipulation of any part of the gene cluster, such as changing promoters or swapping modules, can be performed using the kanamycin resistance and galK cassette, as described below. Cultures of *Myxococcus xanthus* containing the epo genes are grown in a number of media and examined for production of epothilones. If the levels of production of epothilones (in particular B or D) are low, then the *M. xanthus*-producing clones are subjected to media development and mutation based strain improvement.

EXAMPLE 3

Process for the Production of Epothilones B and D

A. Production of Epothilone B

I. Flasks

A 1 mL vial of the K111-32-25 strain is thawed and the contents transferred into 3 mL of CYE seed media in a glass tube. This culture is incubated for 72±12 hours at 30° C., followed by the subculturing of 3 mL of this tube culture into 50 mL of CYE media within a 250 mL baffled Erlenmeyer flask. This CYE flask is incubated for 24±8 hours at 30° C., and 2.5 mL of this seed (5% v/v) used to inoculate the epothilone production flasks (50 mL of CTS-TA media in a 250 mL baffled Erlenmeyer flask). These flasks are then incubated at 30° C. for 48±12 hours, with a media pH at the beginning of 7.4. The peak epothilone A titer is 0.5 mg/L, and the peak epothilone B titer is 2.5 mg/L.

II. Fermentors

A similar inoculum expansion of K111-32-25 as described above is used, with the additional step that 25 mL of the 50 mL CYE seed is subcultured into 500 mL of CYE. This secondary seed is used to inoculate a 10 L fermentor containing 9.5 L of CTS-TA, and 1 g/L of sodium pyruvate. The process parameter setpoints for this fermentation are: pH—7.4; agitation—400 rpm; sparge rate—0.15 vvm. These parameters were sufficient to maintain the DO at greater than 80% of saturation. The pH control is provided by addition of 2.5 N sulfuric acid and sodium hydroxide to the cultures. Peak epothilone titers are achieved at 48±8 hours. The peak epothilone A titer is 1.6 mg/L, and the peak epothilone B titer is 5.2 mg/L.

B. Production of Epothilone D

I. Flasks

A 1 mL vial of the K111-40-1 strain (described in a following example) is thawed and the contents transferred into 3 mL of CYE seed media in a glass tube. This culture is incubated for 72±12 hours at 30° C., followed by the subculturing of 3 mL of this tube culture into 50 mL of CYE media within a 250 mL baffled Erlenmeyer flask. This CYE flask is incubated for 24±8 hours at 30° C., and 2.5 mL of this seed (5% v/v) used to inoculate the epothilone production flasks (50 mL of 1x wheat gluten media in a 250 mL baffled Erlenmeyer flask). These flasks are then incubated at 30° C. for 48±12 hours, with a media pH at the beginning of 7.4. The peak epothilone C titer is 1.4 mg/L, and the peak epothilone D titer is 7.2 mg/L.

II. Fermentors

A similar inoculum expansion of K111-40-1 as described above is used, with the additional step that 25 mL of the 50 mL CYE seed is subcultured into 500 mL of CYE. 250 mL of this secondary seed is used to inoculate a 5 L fermentor containing 4.5 L of CTS-TA, with a 1 g/L daily feed of sodium pyruvate. The process parameter setpoints for this fermentation are: pH—7.4; agitation—400 rpm; sparge rate—0.15 vvm. These parameters were sufficient to maintain the DO at greater than 80% of saturation. The pH control is provided by addition of 2.5 N sulfuric acid and sodium hydroxide to the cultures. Peak epothilone titers are achieved at 36±8 hours. The peak epothilone C titer is 0.5 mg/L, and the peak epothilone D titer is 1.6 mg/L.

| CYE Seed Media | |
|---|---|
| Component | Concentration |
| Casitone (Difco) | 10 g/L |
| Yeast Extract (Difco) | 5 g/L |
| $MgSO_4\_7H_2O$ (EM Science) | 1 g/L |
| HEPES buffer | 50 mM |

Sterilized by autoclaving for 30 minutes at 121° C.

| CTS-TA Production Media | |
|---|---|
| Component | Concentration |
| Casitone (Difco) | 5 g/L |
| $MgSO_4\_7H_2O$ (EM Science) | 2 g/L |
| L-alanine, L-serine, glycine | 1 mg/L |
| HEPES buffer | 50 mM |

Sterlized by autoclaving for 30 minutes at 121° C.

| 1x Wheat Gluten Production Media | |
|---|---|
| Component | Concentration |
| Wheat Gluten (Sigma) | 5 g/L |
| $MgSO_4\_7H_2O$ (EM Science) | 2 g/L |
| HEPES buffer | 50 mM |

Sterilized by autoclaving for 45 minutes at 121° C.

EXAMPLE 4

Construction of a Myxococcus Strain with Non-functional epoK Gene

Strain K111-40-1 was constructed from strain K111-32.25 by insertional inactivation of the epoK gene. To construct an epoK mutant, a kanamycin resistance cassette was inserted into the epoK gene. This was done by isolating the 4879 bp fragment from pKOS35-79.85, which contains epoK, and ligating it into the NotI site of pBluescriptSKII+. This plasmid, pKOS35-83.5, was partially cleaved with ScaI, and the 7.4 kb fragment was ligated with the 1.5 kb EcoRI-BamHI fragment containing the kanamycin resistance gene from pBJ180-2, which had the DNA ends made blunt with the Klenow fragment of DNA polymerase I, to yield plasmid pKOS90-55. Finally, the ~400 bp RP4 oriT fragment from pBJ183 was ligated into the XbaI and EcoRI sites to create pKOS90-63. This plasmid was linearized with DraI and electroporated into the *Myxococcus xanthus* strain K111-32.25.

To create a markerless epoK mutation, pKOS35-83.5 was cleaved with ScaI and the 2.9 kb and 4.3 kb fragments were ligated together. This plasmid, pKOS90-101, has an in-frame deletion in epoK. Next the 3 kb BamHI and NdeI fragment from KG2, which had the DNA ends made blunt with the Klenow fragment of polymerase I and contains the kanamycin resistance and galK genes, was ligated into the DraI site of pKOS90-101 to create pKOS90-105. This plasmid was electroporated into K111-32.25 and kanamycin resistant electroporants were selected. To replace the wild type copy of epoK with the deletion, the second recombination event was selected by growth on galactose plates. These galactose resistant colonies are tested for production of epothilone C and D, and a producing strain is designated K111-72. The resulting strain was designated *Myxococcus xanthus* K-111-40-1 and deposited with the American Type Culture Collection, 10801 University Blvd., Manassas, Va. 20110-2209, on Nov. 21, 2000 in compliance with the Budapest Treaty under accession No. PTA-2712. All restrictions on access to this desposit will be irrevocably removed upon issuance of a U.S. patent on this application.

EXAMPLE 5

Addition of matBC

The matBC genes encode a malonyl-CoA synthetase and a dicarboxylate carrier protein, respectively. See An and Kim, 1998, *Eur. J. Biochem.* 257: 395–402, incorporated herein by reference. These two proteins are responsible for the conversion of exogenous malonate to malonyl-CoA inside the cell. The products of the two genes can transport dicarboxylic acids and convert them to CoA derivatives (see U.S. patent application Ser. No. 60/159,060, filed Oct. 13, 1999, incorporated herein by reference). These two genes can be inserted into the chromosome of *Myxococcus xanthus* to increase the cellular concentrations of malonyl-CoA and methymalonyl-CoA to increase polyketide production. This is accomplished by cleaving pMATOP-2 with BglII and SpeI and ligating it into the BglII and SpeI sites of pKOS35-82.1, which contains the tetracycline resistance conferring gene, the Mx8 att site and the *M. xanthus* pilA promoter to drive expression of matBC. This plasmid can be electroporated into *M. xanthus*. Because the pilA promoter is highly transcribed, it may be necessary to insert a weaker promoter in the event that too much MatB and MatC affect cell growth. Alternative promoters include the promoter of the kanamycin resistance conferring gene.

EXAMPLE 6

Mutation of the $KS^Y$ in the Loading Module

The proposed mechanism of initiation of epothilone biosynthesis is the binding of malonate to the ACP of the loading domain and the subsequent decarboxylation by the loading KS domain. The loading KS domain contains a tyrosine at the active site cysteine ($KS^Y$) which renders it unable to perform the condensation reaction. However, it is proposed to still perform the decarboxylation. Recent work with rat fatty acid synthase has shown that a KS domain which contains a glutamine in the active site cysteine ($KS^Q$) increases the decarboxylation by two orders of magnatude whereas changing this amino acid to serine, alanine, asparagine, glycine or threonine resulted in no increase relative to wild type. Therefore, changing the $KS^Y$ to $KS^Q$ may increase the priming of epothilone resulting in an increase in epothilone production. To make the change in strain K111-32.25, the plasmid pKOS39-148 was constructed that has ~850 bp of the epothilone KS loading module coding sequence. The $KS^Q$ mutation was created in this plasmid by site directed mutagenesis. To perform a gene replacement in K111-32.25, the kanamycin resistance and galK genes from KG2 were inserted into the DraI sites of pKOS39-148 to create plasmids pKOS111-56.2A and pKOS111-56.2B. The plasmids differ in their orientation of the kanamycin-galK cassette. These plasmids were electroporated into K111-32.25 and kanamycin resistant colonies were selected to create strains K111-63. To replace the wild type loading module KS, K111-63 was plated on CYE galactose plates, and colonies were screened for the presence of the $KS^Q$ mutation by PCR and sequencing.

EXAMPLE 7

Addition of mtaA

To increase the levels of Ppant transferase protein, the Ppant transferase from *Stigmatella aurantiaca* strain DW4 can be added to K111-32.25. This is done by PCR amplification of mtaA from DW4 chromosomal DNA using the primers 111-44.1 (AAAAGCTTCGGGGCACCTCCTGGCTGTCGGC) (SEQ ID NO:4) and 111-44.4 (GGTTAATTAATCACCCTCCTCCCACCCCGGGCAT) (SEQ ID NO:5). See Silakowski et al., 1999, *J Biol. Chem.* 274(52):37391–37399, incorporated herein by reference. The ~800 bp fragment was cleaved with NcoI and ligated into the pUHE24-2B that had been cleaved with PstI, the DNA ends made blunt with the Klenow fragment of DNA polymerase I, and cleaved with NcoI. This plasmid is designated pKOSI111-54. The mat gene is transferred to plasmid pKOS35-82.1, which contains the tetracycline resistance conferring gene, the Mx8 att site and the *Myxococcus xanthus* pilA promoter to drive expression of mtaA. This plasmid is introduced into *M. xanthus* and integrated into the Mx8 phage attachment site.

EXAMPLE 8

Construction of Promoter Replacement Plasmids

To improve epothilone production levels and to illustrate the wide variety of promoters that can be used to express PKS genes in host cells of the invention, a series of vectors and host cells can be constructed to replace the *Sorangium cellulosum* epothilone PKS gene promoter with other suitable promoters, as described in this example.

A. Construction of Plasmid with Downstream Flanking Region

Cosmid pKOS35-70.8A3 was cut with NsiI and AvrII. The 9.5 kb fragment was ligated with pSL1190 cut with PstI and AvrII to yield pKOS90-13. Plasmid pKOS90-13 is ~12.9 kb. Plasmid pKOS90-13 was cut with EcoRI/AvrII. The 5.1 kb fragment was ligated with pBluescript digested with EcoRI/SpeI to create pKOS90-64 (~8.1 kb). This plasmid contains the downstream flanking region for the promoter (epoA and some sequence upstream of the start codon). The EcoRI site is ~220 bp upstream from the start codon for the epoA gene. The AvrII site is 5100 bp downstream from the EcoRI site.

B. Cloning of Upstream Flanking Region

Primers 90-66.1 and 90-67 (shown below) were used to clone the upstream flanking region. Primer 90-67 is at the 5' end of the PCR fragment and 90-66.1 is at the 3' end of the PCR fragment. The fragment ends 2481 bp before the start codon for the epoA gene. The ~2.2 kb fragment was cut with HindIII. Klenow polymerase was added to blunt the HindIII site. This fragment was ligated into the HincII site of pNEB193. Clones with the proper orientation, those with the EcoRI site at the downstream end of the insert and HindIII at the upstream end of the insert, were selected and named pKOS90-90.

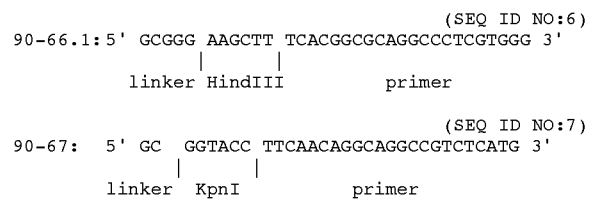

C. Construction of Final Plasmid

Plasmid pKOS90-90 was cut with EcoRI and HindIII. The 2.2 kb fragment was ligated with pKOS90-64 digested with EcoRI/HindIII to create pKOS 90-91 (10.3 kb). Plasmid pKOS90-91 contains the upstream flanking region of the promoter followed by the downstream flanking region in pBluescript. There is a PacI site between the two flanking regions to clone promoters of interest. The galK/$kan^r$ cassette was then inserted to enable recombination into *Myxococcus xanthus*. Plasmid pKOS90-91 was cut with DraI. DraI cuts once in the amp gene and twice in the vector (near the amp gene). Plasmid KG-2 was cut with BamHI/NdeI and Klenow polymerase added to blunt the fragment. The 3 kb fragment (containing galK/$kan^r$ genes) was ligated with the ~9.8 kb DraI fragment of pKOS90-91 to create pKOS90-102 (12.8 kb).

D. Construction of Plasmid with Alternative Leader

The native leader region of the epothilone PKS genes can be replaced a leader with a different ribosome binding site. Plasmid pKOS39-136 (described in U.S. patent application Ser. No. 09/443,501, filed Nov. 19, 1999) was cut with PacI/AscI. The 3 kb fragment containing the leader sequence and part of epoA was isolated and ligated with the 9.6 kb PacI/AscI fragment of pKOS90-102 to create pKOS90-106 (~12.7 kb).

E. Construction of Promoter Replacement Plasmids

I. MTA (myxothiazol) Promoter

The myxothiazol promoter was PCR amplified from *Stigmatella aurantiaca* chromosomal DNA (strain DW4) using primers 111-44.3 and 111-44.5 (shown below). The ~554 bp band was cloned into the HincII site of pNEB193 to create pKOS90-107. Plasmid pKOS90-107 was cut with PstI and XbaI and Klenow filled-in. The 560 bp band was cloned into pKOS90-102 and pKOS90-106 cut with PacI and Klenow filled-in (PacI cuts only once in pKOS90-102 and pKOS90-106). Plasmids were screened for the correct orientation. The MTA promoter/pKOS90-102 plasmid was named pKOS90-114 (13.36 kb) and MTA promoter/pKOS90-106 plasmid was named pKOS90-113 (13.26 kb).

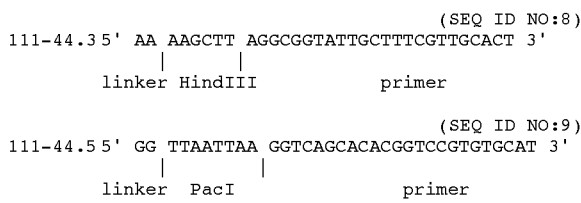

```
                                              (SEQ ID NO:8)
111-44.3 5' AA AAGCTT AGGCGGTATTGCTTTCGTTGCACT 3'
              |       |
           linker  HindIII           primer (SEQ ID NO:9)
111-44.5 5' GG TTAATTAA GGTCAGCACACGGTCCGTGTGCAT 3'
              |        |
           linker   PacI              primer
```

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

II. TA Promoter

The putative promoter for TA along with taA, which encodes a putative transcriptional anti-terminator, was PCR amplified from strain TA using primers 111-44.8 (AAAGATCTCTCCCGATGCGGGAAGGC) (SEQ ID NO:10) and 111-44.9 (GGGGATCCAATGGAAGGGGATGTCCGCGGAA) (SEQ ID NO:11). The ca. 1.1 kb fragment was cleaved with BamHI and BglII and ligated into pNEB193 cleaved with BamHI. This plasmid is designated pKOS111-56.1. The plasmid pKOS111-56.1 was cut with EcoRI and HindIII and Klenow filled-in. The ~1.1 kb band was cloned into pKOS90-102 and pKOS90-106 cut with PacI and Klenow filled-in (PacI cuts only once in pKOS90-102 and pKOS90-106). Plasmids were screened for the correct orientation. The TA promoter/90-102 plasmid was named pKOS90-115 (13.9 kb), and the TA promoter/pKOS90-106 plasmid was named pKOS90-111 (13.8 kb).

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

III. pilA Promoter

Plasmid pKOS35-71B was cut with EcoRI and Klenow filled-in. The 800 bp fragment was cloned into pKOS90-102 and pKOS90-106 cut with PacI and Klenow filled-in. Plasmids were screened for the correct orientation. The pilA promoter/pKOS90-102 plasmid was named pKOS90-120 (13.6 kb), and the pilA promoter/pKOS90-106 plasmid was named pKOS90-121 (13.5 kb).

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

IV. kan Promoter

Plasmid pBJ180-2 was cut with BamHI/BglII and Klenow filled-in. The 350 bp fragment was cloned into pKOS90-102 and pKOS90-106 cut with PacI and Klenow filled-in. Plasmids were screened for the correct orientation. The kan promoter/pKOS90-102 plasmid was named pKOS90-126 (13.15 kb), and the kan promoter pKOS/90-106 plasmid was named pKOS90-122 (13.05 kb).

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

V. So ce90 Promoter

The So ce90 promoter was amplified from So ce90 chromosomal DNA using primers 111-44.6 and 111-44.7 (shown below). The ~900 bp band was cut with PacI and cloned into pNEB193 cut with PacI to create pKOS90-125. Plasmid pKOS90-125 was cut with PacI. The 924 bp band was cloned into pKOS90-102 and pKOS90-106 cut with PacI. Plasmids were screened for the correct orientation. The Soce90 promoter/pKOS90-102 plasmid was named pKOS90-127 (13.6 kb), and the Soce90 promoter/pKOS90-106 plasmid was named pKOS90-128 (13.7 kb).

These plasmids are electroporated into Myxococcus host cells containing the epothilone PKS genes, and kanamycin resistant transformants selected to identify the single crossover recombinants. These transformants are selected for galactose resistance to identify the double crossover recombinants, which are screened by Southern analysis and PCR to identify those containing the desired recombination event. The desired recombinants are grown and tested for epothilone production.

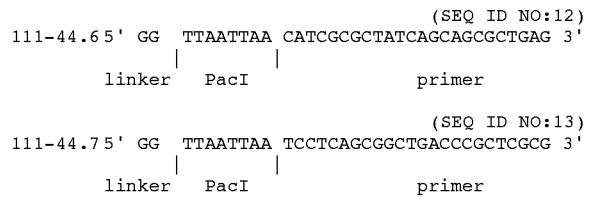

```
                                              (SEQ ID NO:12)
111-44.6 5' GG  TTAATTAA CATCGCGCTATCAGCAGCGCTGAG 3'
               |        |
           linker    PacI            primer (SEQ ID NO:13)
111-44.7 5' GG  TTAATTAA TCCTCAGCGGCTGACCCGCTCGCG 3'
               |        |
           linker    PacI            primer
```

EXAMPLE 9

Construction of a KS2 Knockout Strain

This example describes the construction of an epothilone PKS derivative in which the KS domain of extender module 2 is rendered inactive by a mutation changing the active site cysteine codon to an alanine codon. The resulting derivative PKS can be provided with synthetic precursors (as described in the following Example) to make epothilone derivatives of the invention.

The downstream flanking region of the epothilone PKS gene was PCR amplified using primers 90-103 (5'-AAAAAATGCATCTACCTCGCTCGTGGCGGTT-3') (SEQ ID NO:14) and 90-107.1 (5'-CCCCC TCTAGA ATAGGTCGGCAGCGGTACCCG-3') (SEQ ID NO:15) from plasmid pKOS35-78.2. The ~2 kb PCR product was cut with NsiI/XbaI and ligated with pSL1190 digested with NsiI and SpeI to create pKOS90-123 (~5.4 kb). A ~2 kb PCR fragment amplified with primers 90-105 (5'-TTTTTATGCATGCGGCAGTTTGAACGG-AGATGCT-3') (SEQ ID NO:16) and 90-106 (5'-CCCCCGAATTCTCCCGGAAGGCACACGGAGAC-3') (SEQ ID NO:17) from pKOS35-78.2 DNA was cut with NsiI and ligated with pKOS90-123 digested with NsiI/

EcoRV to create pKOS90-130 (~7.5 kb). When this plasmid is cut with NsiI, and the DNA ends made blunt with the Klenow fragment of DNA polymerase I and religated, plasmid pKOS90-131 is created. To clone the galK/kan^r cassette into this plasmid, plasmid KG-2 is cut with BamHI/NdeI and made blunt with the Klenow fragment of DNA polymerase I. The 3 kb fragment is cloned into the DraI site of pKOS90-131 (DraI cuts three times in the vector) to create plasmid pKOS90-132 (10.5 kb). The NsiI site is used for the purpose of creating the desired change from cysteine to alanine to effect the KS2 knockout. When pKOS90-130 is cut with NsiI, made blunt with the Klenow fragment from DNA polymerase I and re-ligated, the codon for cysteine is replaced with a codon for alanine.

EXAMPLE 10

Modified Epothilones from Chemobiosynthesis

This Example describes a series of thioesters for production of epothilone derivatives via chemobiosynthesis. The DNA sequence of the biosynthetic gene cluster for epothilone from *Sorangium cellulosum* indicates that priming of the PKS involves a mixture of polyketide and amino acid components. Priming involves loading of the PKS-like portion of the loading module with malonyl CoA followed by decarboxylation and loading of the module one NRPS with cysteine, then condensation to form enzyme-bound N-acetylcysteine. Cyclization to form a thiazoline is followed by oxidation to form enzyme bound 2-methylthiazole-4-carboxylate, the product of the loading module and NRPS. Subsequent condensation with methylmalonyl CoA by the ketosynthase of module two provides the equivalent of a diketide, as shown in the following diagram.

The present invention provides methods and reagents for chemobiosynthesis to produce epothilone derivatives in a manner similar to that described to make 6-dEB and erythromycin analogs in PCT Pub. Nos. 99/03986 and 97/02358. Two types of feeding substrates are provided: analogs of the NRPS product, and analogs of the diketide equivalent. The NRPS product analogs are used with PKS enzymes with a mutated NRPS-like domain, and the diketide equivalents are used with PKS enzymes with a mutated KS domain in module two (as described in Example 9).

Loading Module Product Analogs

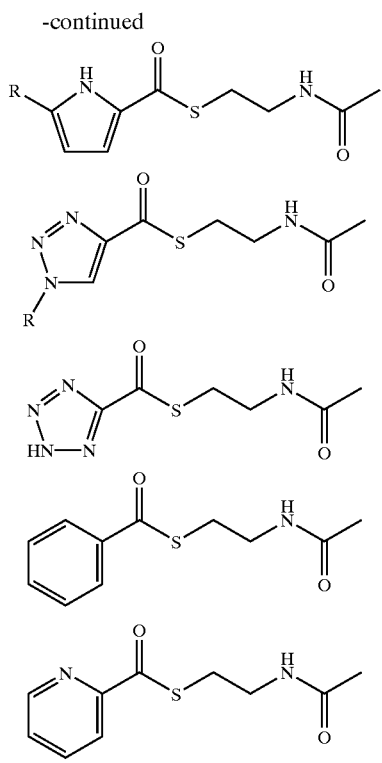

The loading module analogs are prepared by activation of the corresponding carboxylic acid and treatment with N-acetylcysteamine. Activation methods include formation of the acid chloride, formation of a mixed anhydride, or reaction with a condensing reagent such as a carbodiimide.

Diketide Equivalents

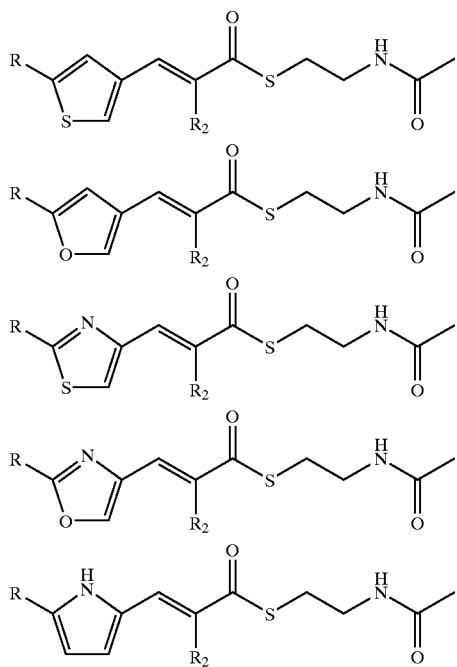

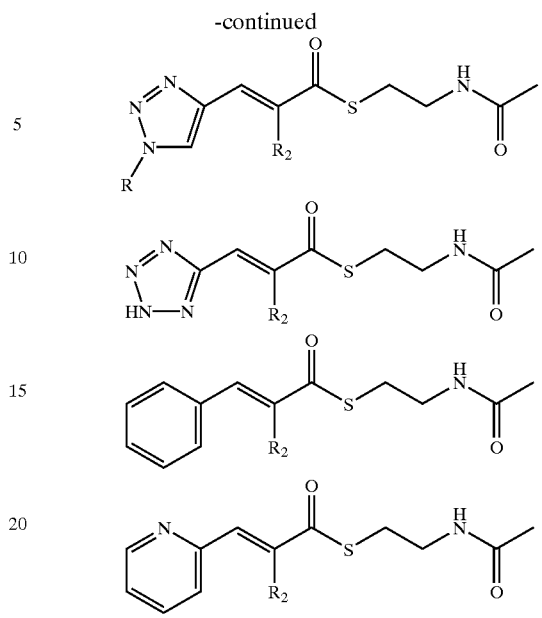

The diketide equivalents are prepared in a three-step process. First, the corresponding aldehyde is treated with a Wittig reagent or equivalent to form the substituted acrylic ester. The ester is saponified to the acid, which is then activated and treated with N-acetylcysteamine.

Illustrative reaction schemes for making loading module product analogs and diketide equivalents follow. Additional compound suitable for making diketide equivalents are shown in FIG. 1 as carboxylic acids (or aldehydes that can be converted to carboxylic acids) that are converted to the N-acylcysteamides for supplying to the host cells of the invention.

A. Thiophene-3-carboxylate N-acetylcy steamine Thioester

A solution of thiophene-3-carboxylic acid (128 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added, and the reaction was allowed to proceed for 12 hours. The mixture was poured into water and extracted three times with equal volumes of ethyl acetate. The organic extracts were combined, washed sequentially with water, 1 N HCl, sat. $CuSO_4$, and brine, then dried over $MgSO_4$, filtered, and concentrated under vacuum. Chromatography on $SiO_2$ using ether followed by ethyl acetate provided pure product, which crystallized upon standing.

B. Furan-3-carboxylate N-acetylcysteamine Thioester

A solution of furan-3-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. $CuSO_4$, and brine, then dried over $MgSO_4$, filtered, and concentrated under vacuum. Chromatography on $SiO_2$ using ether followed by ethyl acetate provided pure product, which crystallized upon standing.

C. Pyrrole-2-carboxylate N-acetylcysteamine Thioester

A solution of pyrrole-2-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. CuSO$_4$, and brine, then dried over MgSO$_4$, filtered, and concentrated under vacuum. Chromatography on SiO$_2$ using ether followed by ethyl acetate provided pure product, which crystallized upon standing.

D. 2-Methyl-3-(3-thienyl)acrylate N-acetylcysteamine Thioester (1) Ethyl 2-methyl-3-(3-thienyl)acrylate: A mixture of thiophene-3-carboxaldehyde (1.12 g) and (carbethoxyethylidene)triphenylphosphorane (4.3 g) in dry tetrahydrofuran (20 mL) was heated at reflux for 16 hours. The mixture was cooled to ambient temperature and concentrated to dryness under vacuum. The solid residue was suspended in 1:1 ether/hexane and filtered to remove triphenylphosphine oxide. The filtrate was filtered through a pad of SiO$_2$ using 1:1 ether/hexane to provide the product (1.78 g, 91%) as a pale yellow oil.

(2) 2-Methyl-3-(3-thienyl)acrylic acid: The ester from (1) was dissolved in a mixture of methanol (5 mL) and 8 N KOH (5 mL) and heated at reflux for 30 minutes. The mixture was cooled to ambient temperature, diluted with water, and washed twice with ether. The aqueous phase was acidified using 1N HCl then extracted 3 times with equal volumes of ether. The organic extracts were combined, dried with MgSO$_4$, filtered, and concentrated to dryness under vacuum. Crystallization from 2:1 hexane/ether provided the product as colorless needles.

(3) 2-Methyl-3-(3-thienyl)acrylate N-acetylcysteamine thioester: A solution of 2-Methyl-3-(3-thienyl)acrylic acid (168 mg) in 2 mL of dry tetrahydrofuran under inert atmosphere was treated with triethylamine (0.56 mL) and diphenylphosphoryl azide (0.45 mL). After 15 minutes, N-acetylcysteamine (0.15 mL) is added and the reaction is allowed to proceed for 4 hours. The mixture is poured into water and extracted three times with equal volumes of ethyl acetate. The organic extracts are combined, washed sequentially with water, 1 N HCl, sat. CuSO$_4$, and brine, then dried over MgSO$_4$, filtered, and concentrated under vacuum. Chromatography on SiO$_2$ using ethyl acetate provided pure product, which crystallized upon standing.

The above compounds are supplied to cultures of host cells containing a recombinant epothilone PKS of the invention in which either the NRPS or the KS domain of module 2 has been inactivated by mutation to prepare the corresponding epothilone derivative of the invention.

The invention having now been described by way of written description and examples, those of skill in the art will recognize that the invention can be practiced in a variety of embodiments and that the foregoing description and examples are for purposes of illustration and not limitation of the following claims.

What is claimed is:

1. A recombinant Myxococcus host cell producing epothilones C and D but not epothilones A and B, said host cell containing a recombinant expression vector that contains a nucleotide sequence that encodes the epothilone polyketide synthase (PKS) of *Sorangium cellulosum*, wherein said epothilone PKS is encoded by the epoA, epoB, epoC, epoD, epoE, epoF, and epoK genes of *Sorangium cellulosum*, and wherein said epoK gene is modified to inactivate expression or modified to encode an inactive epoK gene product.

2. The recombinant host cell of claim 1, wherein said recombinant expression vector is integrated into chromosomal DNA.

3. The recombinant host cell of claim 1 that is *Myxococcus xanthus*.

4. The recombinant host cell of claim 1 that is *Myxococcus xanthus* K111-32.25 (PTA-1700) that has been modified to inactivate an epoK gene.

5. The host cell of claim 4 that is *Myxococcus xanthus* K111-40-1 (PTA-2712).

6. *Myxococcus xanthus* K111-32.25 (PTA-1700).

* * * * *

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: Primer Seq1

<400> SEQUENCE: 1
agcggataac aatttcacac aggaaacagc                30

<210> SEQ ID NO 2
<211> LENGTH: 29
<212> TYPE: DNA
<213> ORGANISM: Artificial Sequence
<220> FEATURE:
<223> OTHER INFORMATION: Primer Mxpil1

<400> SEQUENCE: 2
ttaattaaga gaaggttgca acgggggc                 29

<210> SEQ ID NO 3
<211> LENGTH: 848
<212> TYPE: DNA
<213> ORGANISM: Artificial Sequence
<220> FEATURE:
<223> OTHER INFORMATION: The sequence of the pilA promoter

<400> SEQUENCE: 3
cgacgcaggt gaagctgctt cgtgtgctcc aggagcggaa ggtgaagccg g tcggcagcg      60 ccgcggagat tcccttccag gcgcgtgtca tcgcggcaac gaaccggcgg c tcgaagccg     120 aagtaaaggc cggacgcttt cgtgaggacc tcttctaccg gctcaacgtc a tcacgttgg    180

```
agctgcctcc actgcgcgag cgttccggcg acgtgtcgtt gctggcgaac t acttcctgt        240 ccagactgtc ggaggagttg gggcgacccg gtctgcgttt ctcccccgag a cactgggc         300 tattggagcg ctatcccttc ccaggcaacg tgcggcagct gcagaacatg g tggagcggg        360 ccgcgaccct gtcggattca gacctcctgg ggccctccac gcttccaccc g cagtgcggg        420 gcgatacaga ccccgccgtg cgtcccgtgg agggcagtga gccagggctg g tggcgggct       480 tcaacctgga gcggcatctc gacgacagcg agcggcgcta tctcgtcgcg g cgatgaagc       540 aggccggggg cgtgaagacc cgtgctgcgg agttgctggg cctttcgttc c gttcattcc       600 gctaccggtt ggccaagcat gggctgacgg atgacttgga gcccgggagc g cttcggatg      660 cgtaggctga tcgacagtta tcgtcagcgt cactgccgaa ttttgtcagc c ctggaccca       720 tcctcgccga ggggattgtt ccaagccttg agaattgggg ggcttggagt g cgcacctgg       780 gttggcatgc gtagtgctaa tcccatccgc gggcgcagtg ccccccgttg c aaccttctc      840 ttaattaa                                                                  848

<210> SEQ ID NO 4
<211> LENGTH: 31
<212> TYPE: DNA
<213> ORGANISM: Artificial Sequence
<220> FEATURE:
<223> OTHER INFORMATION: Primer 111-44.1

<400> SEQUENCE: 4
aaaagcttcg gggcacctcc tggctgtcgg c                                        31

<210> SEQ ID NO 5
<211> LENGTH: 34
<212> TYPE: DNA
<213> ORGANISM: Artificial Sequence
<220> FEATURE:
<223> OTHER INFORMATION: Primer 111-44.4

<400> SEQUENCE: 5
ggttaattaa tcaccctcct cccaccccgg gcat                                     34

<210> SEQ ID NO 6
<211> LENGTH: 33
<212> TYPE: DNA
<213> ORGANISM: Artificial Sequence
<220> FEATURE:
<223> OTHER INFORMATION: Primer 90-66.1

<400> SEQUENCE: 6
gcgggaagct ttcacggcgc aggccctcgt ggg                                      33

<210> SEQ ID NO 7
<211> LENGTH: 31
<212> TYPE: DNA
<213> ORGANISM: Artificial Sequence
<220> FEATURE:
<223> OTHER INFORMATION: Primer 90-67

<400> SEQUENCE: 7
gcggtacctt caacaggcag gccgtctcat g                                        31

<210> SEQ ID NO 8
<211> LENGTH: 32
<212> TYPE: DNA
<213> ORGANISM: Artificial Sequence
<220> FEATURE:
<223> OTHER INFORMATION: Primer 111-44.3
```

-continued

```
<210> SEQ ID NO 9
<211> LENGTH: 34
<212> TYPE: DNA
<213> ORGANISM: Artificial Sequence
<220> FEATURE:
<223> OTHER INFORMATION: Primer 111-44.5

<400> SEQUENCE: 9
ggttaattaa ggtcagcaca cggtccgtgt gcat                          34

<210> SEQ ID NO 10
<211> LENGTH: 26
<212> TYPE: DNA
<213> ORGANISM: Artificial Sequence
<220> FEATURE:
<223> OTHER INFORMATION: Primer 111-44.8

<400> SEQUENCE: 10
aaagatctct cccgatgcgg gaaggc                                   26

<210> SEQ ID NO 11
<211> LENGTH: 31
<212> TYPE: DNA
<213> ORGANISM: Artificial Sequence
<220> FEATURE:
<223> OTHER INFORMATION: Primer 111-44.9

<400> SEQUENCE: 11 gggggatccaa tggaagggga tgtccgcgga a                            31

<210> SEQ ID NO 12
<211> LENGTH: 34
<212> TYPE: DNA
<213> ORGANISM: Artificial Sequence
<220> FEATURE:
<223> OTHER INFORMATION: Primer 111-44.6

<400> SEQUENCE: 12
ggttaattaa catcgcgcta tcagcagcgc tgag                          34

<210> SEQ ID NO 13
<211> LENGTH: 34
<212> TYPE: DNA
<213> ORGANISM: Artificial Sequence
<220> FEATURE:
<223> OTHER INFORMATION: Primer 111-44.7

<400> SEQUENCE: 13
ggttaattaa tcctcagcgg ctgacccgct cgcg                          34

<210> SEQ ID NO 14
<211> LENGTH: 31
<212> TYPE: DNA
<213> ORGANISM: Artificial Sequence
<220> FEATURE:
<223> OTHER INFORMATION: Primer 90-103

<400> SEQUENCE: 14
aaaaaatgca tctacctcgc tcgtggcggt t                             31

<210> SEQ ID NO 15
<211> LENGTH: 32
```

```
<212> TYPE: DNA
<213> ORGANISM: Artificial Sequence
<220> FEATURE:
<223> OTHER INFORMATION: Primer 90-107.1

<400> SEQUENCE: 15
ccccctctag aataggtcgg cagcggtacc cg                                32

<210> SEQ ID NO 16
<211> LENGTH: 34
<212> TYPE: DNA
<213> ORGANISM: Artificial Sequence
<220> FEATURE:
<223> OTHER INFORMATION: Primer 90-105

<400> SEQUENCE: 16
tttttatgca tgcggcagtt tgaacggaga tgct                              34

<210> SEQ ID NO 17
<211> LENGTH: 32
<212> TYPE: DNA
<213> ORGANISM: Artificial Sequence
<220> FEATURE:
<223> OTHER INFORMATION: Primer 90-106

<400> SEQUENCE: 17
cccccgaatt ctcccggaag gcacacggag ac                                32
```